United States Patent [19]

Kulesz-Martin

[11] Patent Number: 5,747,650
[45] Date of Patent: *May 5, 1998

[54] P53AS PROTEIN AND ANTIBODY THEREFOR

[75] Inventor: Molly F. Kulesz-Martin, Buffalo, N.Y.

[73] Assignee: Health Research, Inc., Buffalo, N.Y.

[*] Notice: The term of this patent shall not extend beyond the expiration date of Pat. No. 5,688,918.

[21] Appl. No.: 644,456

[22] Filed: May 10, 1996

Related U.S. Application Data

[63] Continuation-in-part of Ser. No. 100,496, Aug. 2, 1993.

[51] Int. Cl.$^6$ .................. C07K 16/22; C07K 16/30; C07K 16/32; C07K 16/06
[52] U.S. Cl. .................. 530/387.7; 530/387.1; 530/389.8; 530/389.1; 530/389.2
[58] Field of Search .................. 530/395, 387.1, 530/388.8, 389.1, 389.2

[56] References Cited

U.S. PATENT DOCUMENTS 4,786,718   11/1988   Weinberg et al. .................. 530/387

FOREIGN PATENT DOCUMENTS

A-0-529 160   3/1993   European Pat. Off.
A-9213970     8/1992   WIPO.

OTHER PUBLICATIONS

Arai, N., et al., (1986) Immunologically Distinct p53 Molecules Generated by Alternative Splicing. Mol. and Cell. Biol. 6, 3232–3239.

Balmain, A., et al. (1982) Cloning and Characterization of the Abundant Cytoplasmic 7S RNA from Mouse Cells. Nucleic Acids Res. 10, 4259–4277.

Bargonetti, J., et al. (1992) Site–Specific Binding of Wild–Type p53 to Cellular DNA is Inhibited by SV40 T Antigen and Mutant p53. Genes & Dev. 6, 1886–1898.

Bischoff, J.R., et al. (1992) Human p53 Inhibits Growth in Schizosaccharomyces Pombe. Mol. and Cell. Biol. 12, 1405–1411.

Burns, P.A., et al. (1991) Loss of Heterozygosity and Mutational Alterations of the p53 Gene in Skin Tumours of Interspecific Hybrid Mice. Oncogene 6, 2363–2369.

Crook, T., et al. (1991) Modulation of Immortalizing Properties of Human Papillomavirus Type 16E7 by p53 Expression. J. Virol. 6, 505–510.

Davies, R., et al. (1993) Antioxidants can Delay Liver Cell Maturation Which in Turn Affects γ–glutamyltranspeptidase Expression. Carcinogen. 14,47–52.

Eliyahu, D., et al. (1988) Meth A Fibrosarcoma Cells Express Two Transforming Mutant p53 Species. Oncogene 3, 313–321.

Farner, G., et al. (1992) Wild–Type p53 Activates Transcription in vitro. Nature 358, 83–86.

Finlay, C.A., et al. (1989) The p53 Proto–Oncogene can Act as a Supressor of Transformation. Cell 57, 1083–1093.

Fontoura, B.M.A. et al. (1992) p53 is Covalently Linked to 5.8S rRNA. Mol. Cell. Biol. 12, 5145–5151.

Foord, O.S., et al. (1991) A DNA Binding Domain is Contained in the C–Terminus of Wild Type p53 Protein. Nucleic Acids Res. 19, 5191–5198.

Foulkes, N.S., et al. (1992) More is Better: Activators and Repressors from the Same Gene. Cell 68, 411–414.

Hainaut, P., et al. (1992) Interaction of Heat–Shock Protein 70 with p53 Translated in vitro evidence for Interaction with Dimeric p53 and for a Role in the Regulation of p53 Conformation. EMBO J. 11, 3513–3520.

Han, K., et al. (1990) Altered Levels of Endogenous Retrovirus–like Sequence (VL30) RNA During Mouse Epidermal Cell Carcinogenesis. Mol. Carcinogenesis 3:75–82.

Han, K., et al. (1992) Altered Expression of Wild–type p53 Tumor Supressor Gene During Murine Epithelial Cell Transformation. Cancer Research 52, 749–753.

Han, K., et al. (1992) Alternatively Spliced p53 RNA in Transformed and Normal Cells of Different Tissue Types. Nucleic Acids Res., 20(8), 1979–1981

Hupp, T.R., et al. (1992) Regulation of the Specific DNA Binding Function of p53. Cell 71, 875–886.

Jenkins, J.R., et al. (1984) Cellular Immortalization by a cDNA Clone Encoding the Transformation–Associated Phosphoprotein p53. Nucleic Acids Res. 12, 5609–5626.

Kastan, M.B., et al. (1991) Participation of p53 Protein in the Cellular Response to DNA Damage. Cancer Research 51, 6304–6311.

Kastan, M.B. et al. (1992) A Mammalian Cell Cycle Checkpoint Pathway Utilizing p53 and GADD45 is Defective in Ataxia–Telangiectasia. Cell 71, 587–597.

Kulesz–Martin, M. et al. (1985) Mouse Cell Clones for Improved Quantitation of Carcinogen–Induced Altered Differentiation. Carcinogenesis 6, 1245–1254.

Kulesz–Martin, M. et al. (1986) Retinoic Acid Enhancement of an Early Step in the Transformation of Mouse Epidermal Cells in vitro. Carcinogenesis 7, 1425–1429.

Kulesz–Martin, M. et al. (1989) Pemphigoid, Pemphigus and Desmoplakin as Antigenic Markers of Differentiation in Normal and Tumorigenic Mouse Keratinocyte Lines. Cell Tissue Kinet. 22, 279–290.

(List continued on next page.)

*Primary Examiner*—Toni R. Scheiner
*Assistant Examiner*—Geetha P. Bansal
*Attorney, Agent, or Firm*—Michael L. Dunn

[57] ABSTRACT

In accordance with the present invention, we have discovered and purified a protein designated herein as p53as, which protein is present in normal cells of a mammal and is essentially identical to known normal growth controlling protein p53 of the same mammal, at least until the final 50 amino acids of the carboxy terminal end of the protein. The invention further includes an antibody specific for protein p53as, which antibody is designated herein as Ab p53as. The antibody may be either a monoclonal or polyclonal antibody and may be specific for p53as of any particular mammal such as mice and humans.

11 Claims, 11 Drawing Sheets

OTHER PUBLICATIONS

Kulesz–Martin, M. et al. (1991) Tumor Progression of Murine Epidermal Cells After Treatment in vitro with 12–O–Tetradecanoylphorbol–13–Acetate or Retinoic Acid. Cancer Research 51, 4701–4706.

Kulesz–Martin, M. et al. (1983) Properties of Carcinogen Altered Mouse Epidermal Cells Resistant to Calcium–Induced Terminal Differentiation. Carcinogen 4, 1367–1377.

Lane, D.P. (1992) p53, Guardian of the Genome. Nature 358, 15–16.

Milne, D.M., et al. (1992) Mutation of the Casein Kinase II Phosphorylation Site Abolishes the Anti–Proliferative Activity of p53. Nucleic Acids Res. 20, 5565–5570.

Milner, J. (1991) The Role of p53 in the Normal Control of Cell Proliferation. Current Opinion in Cell Biology 3, 282–286.

Milner, J. (1984) Different Forms of p53 Detected by Monoclonal Antibodies in Non–Dividing and Dividing Lymphocytes. Nature 20, 143–145.

Milner, J. et al. (1991) Cotranslation of Activated Mutant p53 with Wild Type Drives the Wild–Type p53 Protein into the Mutant Conformation. Cell 65, 765–774.

Momand, J., et al. (1992) The mdm–2 Oncogene Product forms a Complex with the p53 Protein and Inhibits p53–Mediated Transactivation. Cell 69, 1237–1245.

Nigro, J.M., et al. (1992) Human p53 and CDC2Hs Genes Combine to Inhibit the Proliferation of Saccharomyces Cerevisiae. Mol. and Cell Biol. 12, 1357–1365.

Oren, M. et al. (1983) Molecular Cloning of a cDNA Specific for the Murine p53 Cellular Tumor Antigen. Proc. Natl. Acad. Sci. USA, 80, 56–59.

Prives, C., et al. (1993) The p53 Tumor Suppressor Protein: Meeting Review. Genes & Dev. 7:529–534.

Ro, Y.S., et al. (1993) p53 Protein Expression in Benign and Malignant Skin Tumours. Br. J. Dermatol. 12, 237–241.

Ruggeri, B., et al. (1991) Alterations of the p53 Tumor Suppressor Gene During Mouse Skin Tumor Progression. Cancer Research 51, 6615–6621.

Schneider, B.L., et al. (1993) 7,12–Dimethylbenz[α]anthracene–Induced Mouse Keratinocyte Transformation Without Harvey ras Protooncogene Mutations. J. Invest. Dermatology, 101:595–599, 1993.

Seto, E., et al. (1992) Wild–Type p53 Binds to the TAT-A–Binding Protein and Represses Transcription. Proc. Natl. Acad. Sci. 89, 12028–12032.

Soussi, T., et al. (1990) Structural Aspects of the p53 Protein in Relation to Gene Evolution. Oncogene 5, 945–952.

Stenger, J.E., et al. (1992) Formation of Stable p53 Homotetramers and Multiples of Tetramers. Mol. Carcinogen. 5, 102–106.

Stephen, C.W., et al. (1992) Mutant Conformation of p53. Precise Epitope Mapping Using a Filamentous Phage Epitope Library. J. Mol. Biol. 225.577–583.

Sturzbecher, H.S., et al. (1992) A C–Terminal α–Helix Plus Basic Region Motif is the Major Structural Determinant of p53 Tetramerization. Oncogene 7, 1513–1523.

Vogelstein, B. (1990) A Deadly Inheritance. Nature 348, 681–682.

Vogelstein, B., et al. (1992) p53 Function and Dysfunction. Cell 70, 523–526.

Wade–Evans, A., et al. (1985) Precise Epitope Mapping of the Murine Transformation–Associated Protein, p53. EMBO J. 4,699–706.

Weintraub, H., et al. (1991) The MCK Enhancer Contains a p53 Responsive Element. Proc. Natl. Acad. Sci. 88, 4570–4571.

Wolf, D., et al. (1985) Isolation of a Full–Length Mouse cDNA Clone Coding for an Immunologically Distinct p53 Molecule. Mol. and Cell Biol. 51, 127–132.

Wolf, D., et al. (1984) Reconstitution of p53 Expression in a Nonproducer Ab–MuLV–Transformed Cell Line by Transfection of a Functional p53 Gene. Cell 38, 119–126.

Yewdell, J.W. et al. (1986) Monoclonal Antibody Analysis of p53 Expression in Normal and Transformed Cells. J. Virol. 59, 444–452.

Yonish–Rouach, E., et al. (1993) p53–Mediated Cell Death: Relationship to Cell Cycle Control. Mol. and Cell. Biol. 13, 1415–1423.

Yonish–Rouach, E., et al. (1991) Wild–Type p53 Induces Apoptosis of Myeloid Leukaemic Cells that is Inhibited by Interleukin–6. Nature 352, 345–347.

Zambetti, G.P., et al. (1992) Wild–Type p53 Mediates Positive Regulation of Gene Expression Through a Specific DNA Sequence Element. Genes & Dev. 6, 1143–1159.

Midgely et al. J. Cell Science 101:(1992) pp. 183–189, 1992.

Banks et al. Eur. J. Biochem. 159:(1986) pp. 529–534, 1986.

Gannon et al. EMBO J. 9:pp. 1595–1602 (1990).

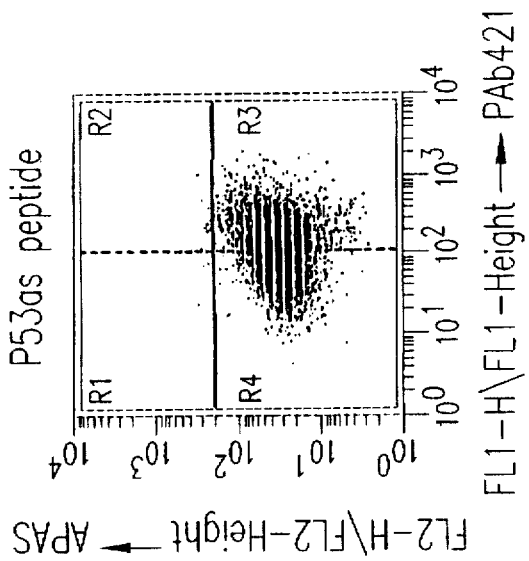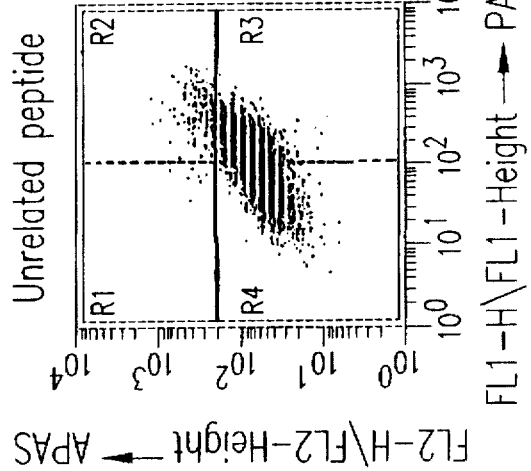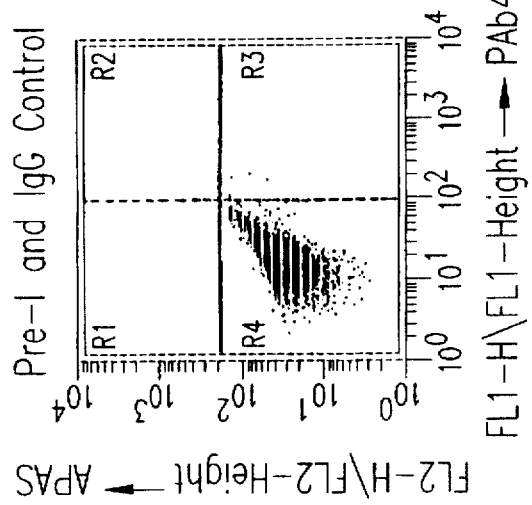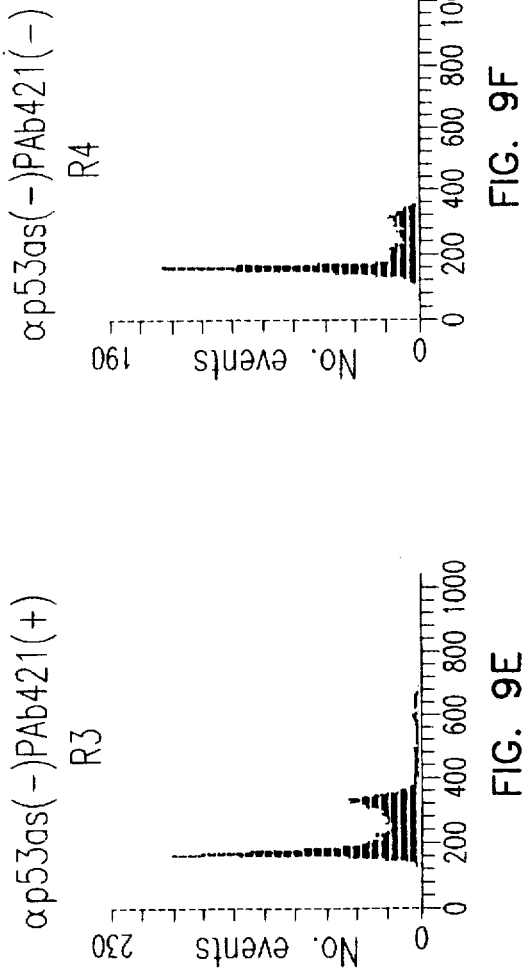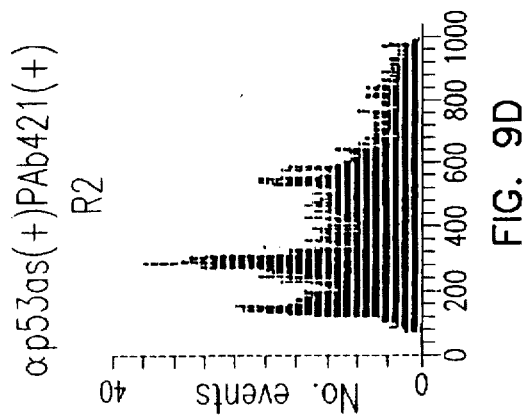

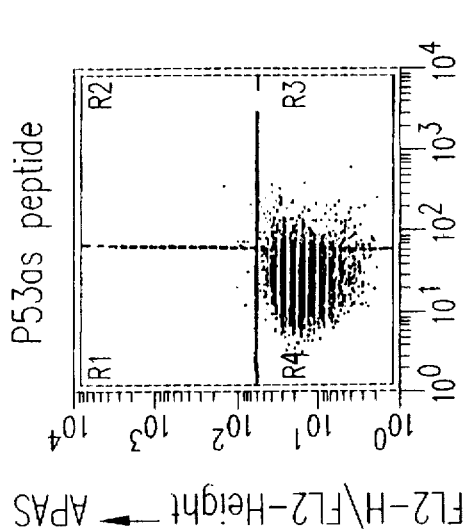
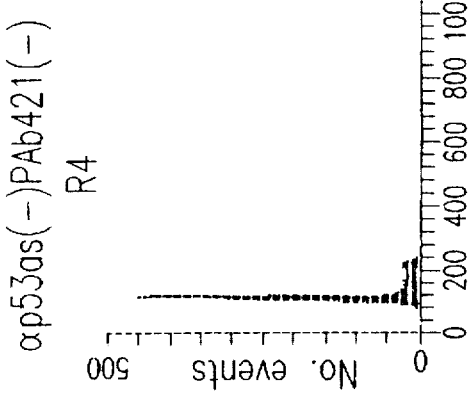
FIG. 10A
FIG. 10D
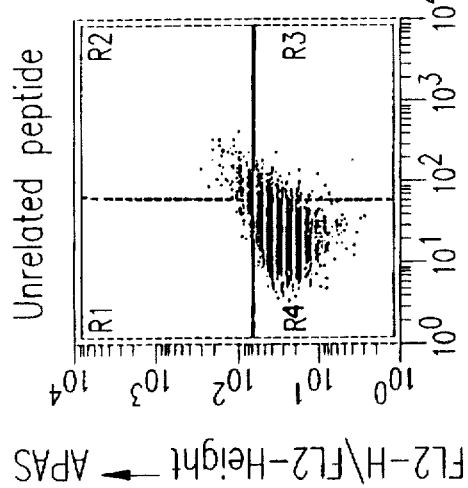
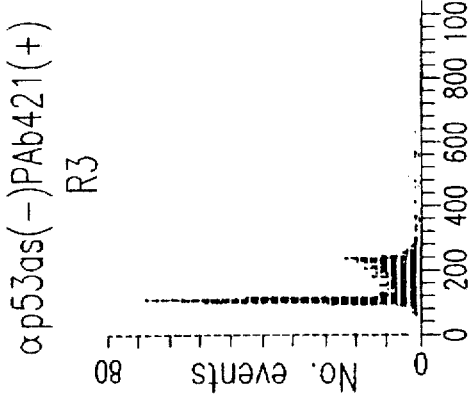
FIG. 10B
FIG. 10E
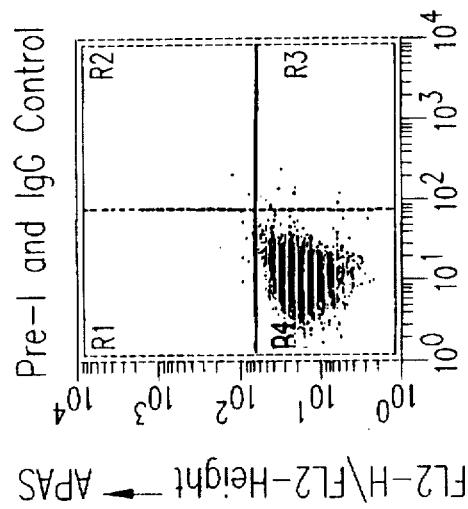
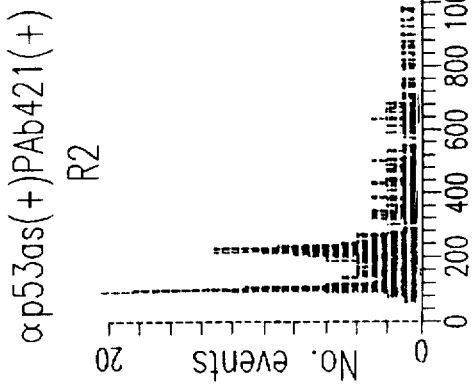
FIG. 10C
FIG. 10F

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
       ( A ) LENGTH: 17
       ( B ) TYPE: amino acids
       ( C ) STRANDEDNESS: Not Relevant
       ( D ) TOPOLOGY: Not Relevant ( i i ) MOLECULE TYPE: peptide ( i i i ) HYPOTHETICAL: no ( i v ) ANTI-SENSE: no ( v ) FRAGMENT TYPE: n/a ( v i ) ORIGINAL SOURCE:
       ( A ) ORGANISM: mouse
       ( B ) STRAIN: n/a
       ( C ) INDIVIDUAL ISOLATE: n/a
       ( D ) DEVELOPMENTAL STAGE: n/a
       ( E ) HAPLOTYPE: n/a
       ( F ) TISSUE TYPE: n/a
       ( G ) CELL TYPE: n/a
       ( H ) CELL LINE: n/a
       ( I ) ORGANELLE: n/a ( v i i ) IMMEDIATE SOURCE: sequenced from cDNA clone from mouse
             epidermal cell RNA, Genbank Accession #M13874
       ( A ) LIBRARY: plasmid p6.3
       ( B ) CLONE:

( v i i i ) POSITION IN GENOME:
       ( A ) CHROMOSOME/SEGMENT: 11
       ( B ) MAP POSITION: p53 gene
       ( C ) UNITS:

( i x ) FEATURE: n/a
       ( A ) NAME/KEY:
       ( B ) LOCATION:
       ( C ) IDENTIFICATION METHOD:
       ( D ) OTHER INFORMATION:

( x ) PUBLICATION INFORMATION:
       ( A ) AUTHORS: Kulesz-Martin et al.
       ( B ) TITLE: Endogenous p53 Protein Generated From Wild
             Type Alternatively Spliced P53 RNA in Mouse
       ( C ) JOURNAL: Mol. Cell. Biol.
       ( D ) VOLUME: 14
       ( E ) ISSUE: 3
       ( F ) PAGES: 1698-1708
       ( G ) DATE: March, 1994
       ( A ) AUTHORS: Han, K.A. and Kulesz-Martin, M.F.
       ( B ) TITLE: Alternatively Spliced p53 RNA in Transformed
             and Normal Cells of Different Tissue Types
       ( C ) JOURNAL: Nucleic Acids Res.
       ( D ) VOLUME: 20
       ( E ) ISSUE: 8
       ( F ) PAGES: 1979-1981
       ( G ) DATE: 1992
       ( A ) AUTHORS: Arai, N. et al.
       ( B ) TITLE: Immunologically Distinct p53 Molecules Generated
             by Alternative Splicing
       ( C ) JOURNAL: Mol. and Cell. Biol.
       ( D ) VOLUME: 6
       ( E ) ISSUE:
       ( F ) PAGES: 3232-3239
       ( G ) DATE: 1986
       ( H ) DOCUMENT NUMBER:
       ( I ) FILING DATE:
       ( J ) PUBLICATION DATE:
       ( K ) RELEVANT RESIDUES IN SEQ ID NO:

( x i ) SEQUENCE DESCRIPTION: SEQ ID NO: 1:

Leu Gln Pro Arg Ala Phe Gln Ala Leu Ile Lys Glu Glu Ser Pro Asn
 1               5                       10                  15
Cys ( 2 ) INFORMATION FOR SEQ ID NO: 2:

( i ) SEQUENCE CHARACTERISTICS:
        ( A ) LENGTH: 33
        ( B ) TYPE: Nucleic Acids
        ( C ) STRANDEDNESS: Unknown
        ( D ) TOPOLOGY: Unknown ( i i ) MOLECULE TYPE: Oligonucleotide ( i i i ) HYPOTHETICAL:

( i v ) ANTI-SENSE:

( v ) FRAGMENT TYPE:

( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: Genbank Accession #X54156, Locus HUM P53G
        ( A ) LIBRARY:
        ( B ) CLONE:

( v i i i ) POSITION IN GENOME:
        ( A ) CHROMOSOME/SEGMENT: 17
        ( B ) MAP POSITION: p53 gene 17593- 17613
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 2:

ATCGAAGCTT GAGATGTTCC GAGAGAGCTG AAT        33

( 2 ) INFORMATION FOR SEQ ID NO: 3:

( i ) SEQUENCE CHARACTERISTICS:
        ( A ) LENGTH: 31
        ( B ) TYPE: Nucleic acids
        ( C ) STRANDEDNESS: unknown
        ( D ) TOPOLOGY: unknown ( i i ) MOLECULE TYPE: oligonucleotide ( i i i ) HYPOTHETICAL:

( i v ) ANTI-SENSE:

( v ) FRAGMENT TYPE:

( v i ) ORIGINAL SOURCE:
    ( A ) ORGANISM: Human
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE: Genbank Accession #54156, Locus HUMP53G
    ( A ) LIBRARY:
    ( B ) CLONE:

( v i i i ) POSITION IN GENOME:
    ( A ) CHROMOSOME/SEGMENT: 17
    ( B ) MAP POSITION: p53 gene 18774- 18794
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 3:

ATCGTCTAGA GCTTCTGACG CACACCTATT G         31

( 2 ) INFORMATION FOR SEQ ID NO: 4:

( i ) SEQUENCE CHARACTERISTICS:
        ( A ) LENGTH: 20
        ( B ) TYPE: Amino Acids
        ( C ) STRANDEDNESS: unknown
        ( D ) TOPOLOGY: unknown ( i i ) MOLECULE TYPE: Peptide ( i i i ) HYPOTHETICAL: deduced from intron 10 sequences p53 gene ( i v ) ANTI-SENSE:

( v ) FRAGMENT TYPE:

( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: deduced translation from nucleotides in
            Genbank nucleic acid database accession #54156,
            Locus HSP53G (B) CLONE:

(viii) POSITION IN GENOME:
                (A) CHROMOSOME/SEGMENT: 17
                (B) MAP POSITION: p53 gene, at 18530 to 18589
                (C) UNITS:

(ix) FEATURE: n/a
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 4:

```
Arg Glu Lys Gly His Arg Pro Ser His Ser Cys Asp Val Ile Ser Pro
 1               5                  10                  15

Pro Cys Phe Cys
            20
```

(2) INFORMATION FOR SEQ ID NO: 5:

(i) SEQUENCE CHARACTERISTICS:
                (A) LENGTH: 16
                (B) TYPE: Amino Acids
                (C) STRANDEDNESS: unknown
                (D) TOPOLOGY: unknown (ii) MOLECULE TYPE: peptide (iii) HYPOTHETICAL:

(iv) ANTI-SENSE:

(v) FRAGMENT TYPE:

(vi) ORIGINAL SOURCE: mouse glucocorticoid receptor sequence
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:

```
           ( C ) JOURNAL:
           ( D ) VOLUME:
           ( E ) ISSUE:
           ( F ) PAGES:
           ( G ) DATE:
           ( H ) DOCUMENT NUMBER:
           ( I ) FILING DATE:
           ( J ) PUBLICATION DATE:
           ( K ) RELEVANT RESIDUES IN SEQ ID NO:

( x i ) SEQUENCE DESCRIPTION: SEQ ID NO: 5:

Gly  Arg  Asn  Asp  Cys  Ile  Ile  Asp  Lys  Ile  Arg  Arg  Lys  Asn  Cys  Asp
 1              5                   10                       15
```

P53AS PROTEIN AND ANTIBODY THEREFOR

This is a continuation-in-part of U.S. patent application Ser. No. 08/106,496, filed Aug. 2, 1993.

This work was supported by a grant from the National Institutes of Health (CA 31101). The United States Government may have certain rights in the invention.

BACKGROUND OF THE INVENTION

This invention relates to p53 protein and variations thereof, and more particularly relates to antibodies to such variations.

The p53 gene which encodes for p53 protein is defective in over half of all human cancers. It is furthermore significant because introduction of a normal p53 gene into a variety of cancer cells arrests their growth. Thus, defects in the p53 gene product (that is, the p53 protein) are common in many cancers and, if corrected, could inhibit cancer cell growth. In many human cancers, the p53 protein is inactive because of mutation of the p53 gene. Replacement of a single amino acid can be sufficient to change the normal folding of the p53 protein, making it inactive as a growth control gene. In certain cells, the folding of a mutant p53 protein can be stabilized in the normal conformation by binding to cellular factors, suggesting that it may be possible to create peptides which bind to p53 protein and cause it to be maintained in the normal conformation (conformations are forms of a protein created due to folding; conformations can change without (or with) changes in amino acid sequence). The normal conformation has the tumor suppressor effect. Cells expressing primarily mutant p53 conformation give rise to aggressive tumors at high frequency while cells which primarily express p53 protein in a normal conformation give rise to slow-growing tumors at low frequency.

To date, many studies of p53 protein and its function have relied upon a specific (PAb421) antibody thereto. Most p53 proteins studied using in vitro (cell-free) assays of binding to DNA or modulation of transcription have used a p53 protein purified using PAb421, and thus excluding other proteins. While p53 binding detectable to date is sequence specific, it is low in efficiency. A model has been proposed for activation of p53 protein for binding to DNA by modifications at the carboxyl terminus of p53, Hupp et al. (1992) "Regulation of the specific DNA binding function of p53", Cell 71, 875-886, as shown in FIG. 1. Modifications include proteolysis (loss of carboxyl terminal amino acids, phosphorylation of serine in this region or binding of PAb421 antibody within this region.

It has been shown that p53as RNA exists in normal mouse cells and tissues and in tumor cells (Han et al. (b) (1992), "Alternatively spliced p53 RNA in transformed and normal cells of different tissue types", Nucleic Acids Res., 20(8), 1979–1981; however, no protein has heretofore been found which is encoded by that RNA.

BRIEF DESCRIPTION OF THE INVENTION

In accordance with the present invention, we have discovered and purified a protein designated herein as p53as, E. Coli containing a plasmid containing a sequence which encodes a p53as, has been deposited with ATCC Rockwell, Md. having ATCC Accession Number 69657. A form of p53as is naturally present in normal cells of at least some mammals, and is essentially identical to known normal growth controlling protein p53, at least until the final 50 amino acids and preferably until the final 30 amino acids of the carboxy terminal end of the protein. "Essentially identical" means at least 80% and preferably at least 90% sequential correspondence with p53. It should be noted that mouse p53 has an 81% identity at the protein level, with a highly acidic N-terminus, basic C-terminus and a central region containing uncharged amino acids.

The final 50 amino acids of p53as protein proximate the carboxy terminus of the p53as protein, are at least partly different than the final 50 amino acids of p53 protein. The difference is believed to be at least in part due to different amino acid sequences in the two proteins proximate the carboxy termination of the protein and may also be partly due to a longer or shorter p53as amino acid chain when compared with p53. It is believed that the most common and probable final few amino acids at the carboxy termination of naturally occurring p53as contain the sequences SPNC and SPPC. p53as has been found to function as a growth regulator in all mammals tested regardless of whether or not p53as has been found to naturally occur in the mammal.

It is to be understood that p53as may be of natural or synthetic form, provided that, at a minimum, terminal amino acids differ from the 50 terminal amino acids of p53 so that the modified product will act the same as active p53 protein and is functionally equivalent to mouse p53as protein.

In general, it can be stated that p53as is functionally the same as p53 except that a p53as lacks the negative regulatory domain for p53 sequence specific DNA binding which is found within the last 50 amino acids at the p53 c terminus. The negative regulatory domain of p53 negates p53 sequence specific binding in certain cellular environments which in turn causes p53 to lose activity. p53as lacks the negative regulatory domain and thus remains active in similar cellular environments.

To obtain a p53as, the terminal amino acids of p53 are preferably modified, i.e., there is at least some substitution, as opposed to simple truncation.

The invention further includes an antibody specific for a p53as protein, which antibody is designated herein as Ab p53as. The antibody may be either a monoclonal or polyclonal antibody and may be specific for any particular p53as or p53as of synthetic form.

Figure 1:
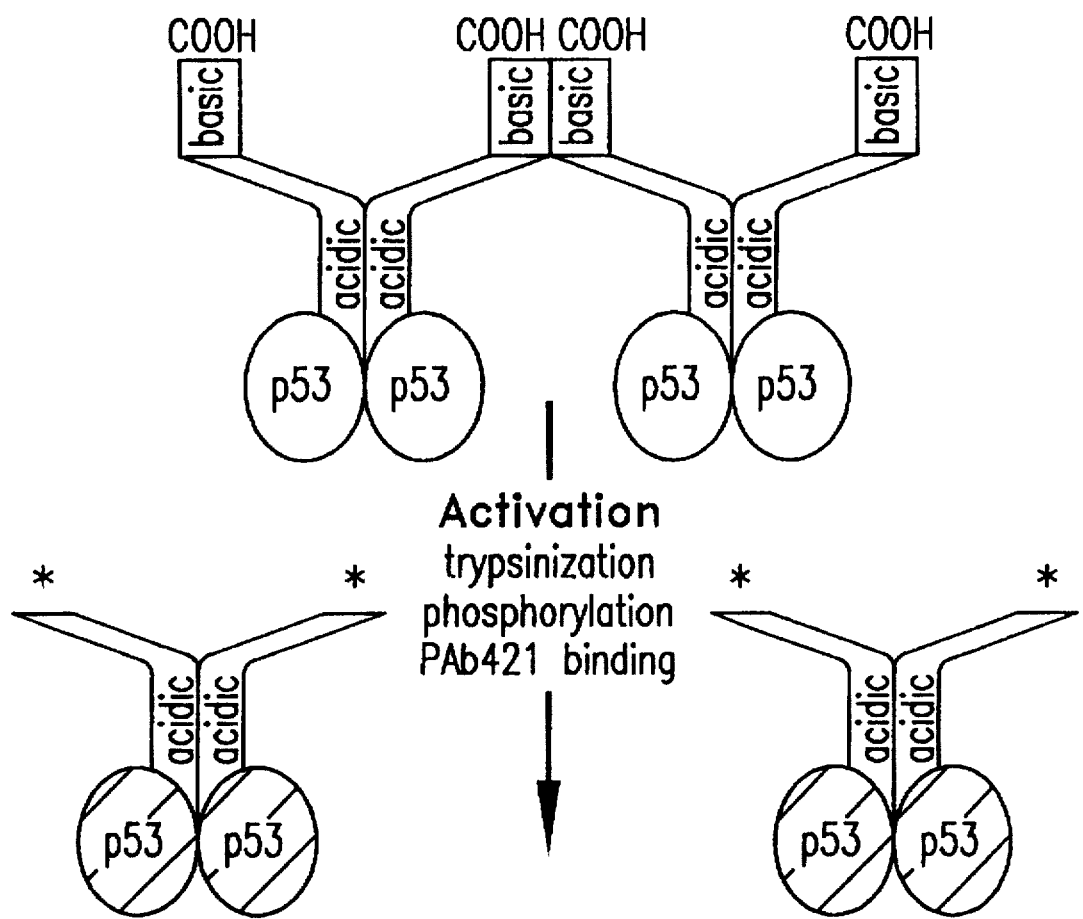
FIG. 1 shows a diagram for a proposed mechanism of activation of DNA binding by p53 protein.

Fold-increase in signals detectable by densitometry, adjusted for loading by comparison with 7S RNA, are indicated.

FIGS. 9A through 9F show expression of p53 (Pab421) and p53as antigen activities in 291.05RAT carcinoma cells. Cells were treated with 0.5 nM actinomycin D for 2 days and harvested by trypsinization. Cells were permeabilized and stained in suspension with anti-p53as and PAb421 antibodies (in the same tube) in all cases shown except for the primary antibody control (upper left). In the 3 dot plots at top, FIGS. 9A through 9C, the FL1 fluorescence intensity on the x-axis was FITC (green), used to visualize Pab421 reactivity, and the FL2 fluorescence intensity on the Y-axis was phycoerythrin (red) used to visualize anti-p53as reactivity. Prior to incubation with cells, the anti-p53as antibody was exposed to either p53as peptide, which competitively removed the specific anti-p53as reactivity, or to an unrelated peptide, which controlled for nonspecific binding to peptide, leaving only specific reactivity to p53as protein. Events collected by flow cytometry were single cells only as described in Experimental Procedures. Coordinates were set on total cell data based on IgG2a and pre-immune controls to delineate four regions: negative for both antibodies (R4), positive for anti-p53as only (R1), positive for PAb421 and anti-p53as (R2) and positive for PAb421 only (R3). After collecting a file of 10,000 total events per tube (as shown in the 3 dot plots at top), additional gates were set to exclude negative cells (R4) and to maximize the collection of cells positive for PAb421 (histogram R3 shown), or to exclude negative cells (R4) and cells positive only for PAb421 (R3) in order to maximize the collection of cells positive for anti-p53as (R2). The cell cycle distribution of events from each region (R2 through R4, FIGS. 9D through 9F) is shown in the 3 histograms at bottom. The numbers of cells in each region expressed as a percentage of the total cells were: unrelated peptide, R1, 0.02, R2, 1.7, R3, 17 and R4, 79 (numbers may not add to 100 due to rounding error and to a negligible number of events outside the windows included in the analysis); p53as peptide, R1, 0.02, R2, 0.05, R3, 19, R4, 79. Percentages of cells in each phase of the cell cycle and total events (n) for each region in the histograms shown were: R2, G0/G1, 19, S, 13, G2/M, 25 and >G2/M, 43, n=2224; R3, G0/G1, 38, S, 16, G2/M, 33 and >G2/M, 12, n=6879; R4, G0/G1, 60, S, 18, G2/M, 21 and >G2/M, 1, n=7925.

FIGS. 10A through 10F show expression of p53 (Pab421) and p53as antigen activities in 291.05RAT carcinoma cells. Cells were cultured under low Ca$^{2+}$ conditions (LC) which favored cell growth. Treatment and analysis was the same as for carcinoma cells presented in FIGS. 9A through 9F. The dot plots are shown in FIGS. 10A through 10C and the histograms are shown in FIGS. 10D through 10F. The numbers of cells in each region expressed as a percentage of the total cells were: unrelated peptide, R1, 1.2, R1, 2, R3, 4 and R4, 92; p53as peptide, R1, 0.1, R2, 0.1, R3, 5, R4, 94. Percentages of control cells in each phase of the cell cycle and total events (n) for each region in the histograms shown were: R2, G0/G1, 29, S, 11, G2/M, 35 and >G2/M, 25, n=1074; R3, G0/G1, 61, S, 15, G2/M, 22 and >G2/M, 2, n=1974; R4, G0/G1, 78, S, 11, G2/M, 11 and >G2/M, 0.04, n=9194.

DETAILED DESCRIPTION OF THE INVENTION

In accordance with the present invention, the inventor has now discovered a novel form of a wild type (normal) p53 protein and demonstrated that it is present in nontransformed mouse cell strains and mouse squamous cell carcinomas. Designated p53as, (alternatively spliced p53) it arises from a normal variation in processing of the p53 messenger RNA (mRNA).

It has been previously demonstrated that a wild type alternatively spliced p53 (p53as) RNA exists in mouse cultured cells and normal mouse tissue at approximately 25 to 33% of the major p53 RNA form. It has been found that the alternative RNA transcript is 96nt longer than the major transcript due alternative slicing of intron 10 sequences. It has now been determined that p53as protein exists in nontransformed and malignant epidermal cells and is localized to the nucleus along with the major p53 protein. The protein expected to be generated from the p53as transcript is 9 amino acids shorter than the major p53 protein and has 17 different amino acids at the carboxyl terminus. In addition, p53as protein is preferentially expressed during the G2 phase of the cell cycle and in cells with greater than G2 DNA content, compared to the major p53 protein which is preferentially expressed in G1. The p53as immunoreactivity is elevated and shifted to the G1 phase of the cell cycle following actinomycin D treatment of nontransformed but not malignant cells. In view of the dimerization and tetramerization of p53 protein which may be necessary for its DNA binding and transcriptional activation activities, the presence of p53as protein in cells has important implications for understanding the physiological function(s) of the p53 gene.

It is believed that the p53as protein, similar to p53, may be used in studying cell growth and maturation, detecting normal versus abnormal cell growth and may be used to normalize cell growth of abnormally growing cells.

Hereafter the p53 protein recognized to date will be referred to as the major form of p53 or simply p53; this does not rule out the existence of a cell type in which p53as may be present in relatively higher amounts than p53. DNA is transcribed to RNA which is then processed by removal of segments called introns to give the mature messenger RNA which encodes protein. In alternative splicing, a segment of an intron is retained in the coding sequence (called an alternatively spliced messenger RNA) and makes a protein which is partly different from the major form of the protein. The p53as sequence found in mouse normal and tumor cells has 17 different amino acids at the carboxyl terminus of the p53 protein (out of a total of 390 amino acids in the major p53 form). This unique sequence was used to generate antibody specific to mouse p53as. The antibody does not cross react with the major p53 protein. It is novel, in that no other antibody reactive with p53as has been reported or made based on available knowledge.

Figure 2A:
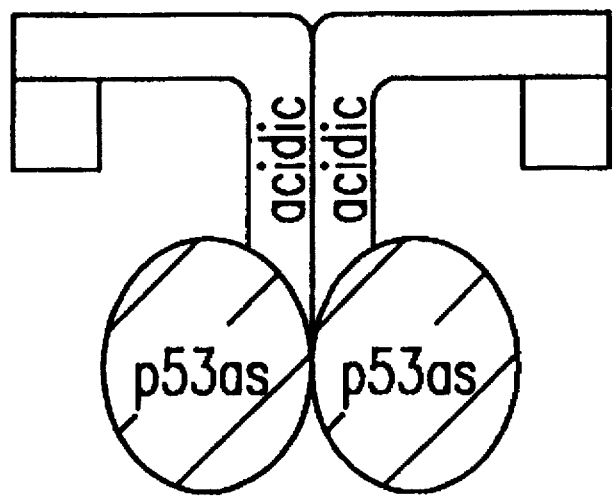
FIGS. 2A and 2B show diagrams for a proposed model for p53as protein activity.
Figure 2B:
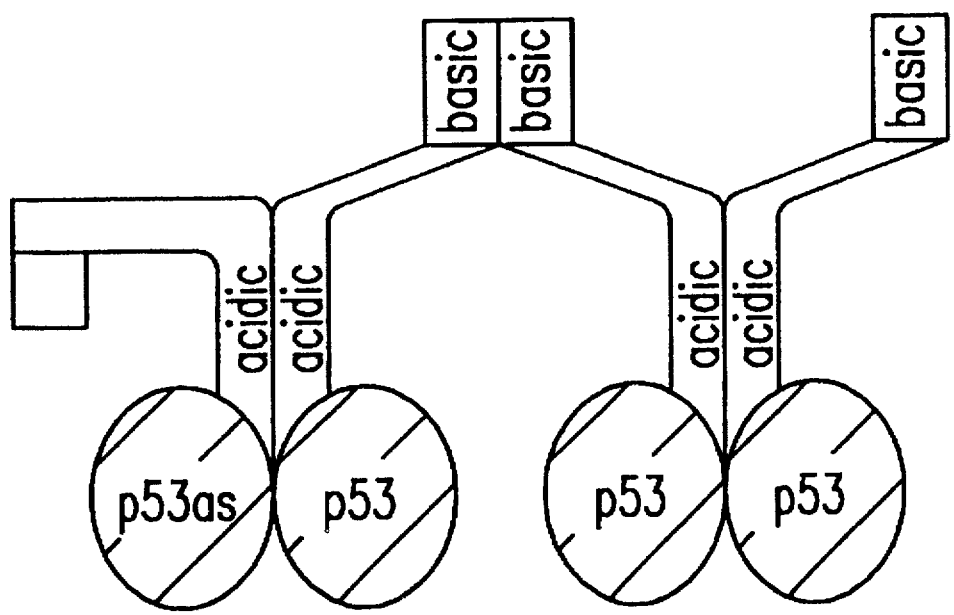

The p53as protein, by virtue of the replacement of 17 amino acids and loss of 9 amino acids within the carboxyl terminus, already harbors changes in this "DNA activation" region. p53as protein in complex with itself (dimer formation is possible due to retention of acidic residues known to be important for dimerization of p53 protein) or in complex with the major p53 protein will bind to DNA and modulate transcription of specific target genes with altered, perhaps greater, efficiency than homodimers or homotetramers of the major p53 protein only (see FIG. 2).

Polyclonal and monoclonal antibodies to mouse p53 available prior to the present invention do not specifically recognize p53as. These include PAb246 which recognizes mouse p53 in its normal folding state, PAb240 which recognizes certain mutant p53 proteins, PAb421 which recognizes the carboxyl terminal amino acids replaced or lost in p53as. Similarly, human p53 is recognized by monoclonal and polyclonal antibodies. No report of a human p53 generated by alternative splicing at the carboxyl terminus has been reported and no specific antibody to human p53as is available.

The development of antibody to p53as protein in accordance with the present invention, permits studies of whether p53 protein and p53as protein associate in the cell, and will permit in vitro studies of the efficiency of DNA binding and transcriptional regulation of complexes between p53 and p53as proteins. Such antibodies may also permit detection of cells having normal growth from cells having abnormal accelerated growth.

Mouse p53as Peptide

Alternative splicing of mouse p53 RNA results in insertion of 96nt from intron 10 of the p53 gene. These 96nt encode (in frame) 17 amino acids which are distinct from those in the major p53 RNA form, beginning at residue 365 and extending to residue 381, followed by a stop codon which results in truncation by 9 amino acids. This 17 amino acid peptide of alternatively spliced mouse p53, called mouse p53as peptide is: LQPRAFQALIKEESPNC. It was produced by standard synthesis, tested for authenticity and is stored in the laboratory. Details and procedures are as follows:

During the sequencing of p53 cDNA from the tumor and normal cells of the mouse cloned keratinocyte model the inventor herein detected an alternatively spliced p53 mRNA in which 96nt of the 3' end of intron 10 are inserted between nt 1091 and nt 1092 of the mouse p53 gene (1 being adenine of the first ATG codon; (Han et al. (b) (1992), supra) P53 mRNA was first cloned as a mutant p53 cDNA (M-8) from a chemically transformed fibroblast cell line by Wolf et al., (1985) "Isolation of a full-length mouse cDNA clone coding for an immunologically distinct p53 molecule", *Mol. and Cell. Biol.* 51, 127–132; Arai et al., supra, reported the sequence of this p53 cDNA variant, confirming its origin by alternative splicing. It appeared to be specific to this tumor cell lineage because it was undetectable in a nontransformed helper T-cell cDNA library. However, it has been demonstrated that wild type alternatively spliced 53 RNA is expressed in normal cells and tissues at about 25 to 33% of the major p53 RNA form (Han et al., (b) (1992) supra). In addition, it is present at approximately the same ratio in the two independently-derived epidermal carcinoma lines which overexpress p53 RNA (noted above), and thus appeared to be coordinately elevated with the major form of p53.

Figure 3:
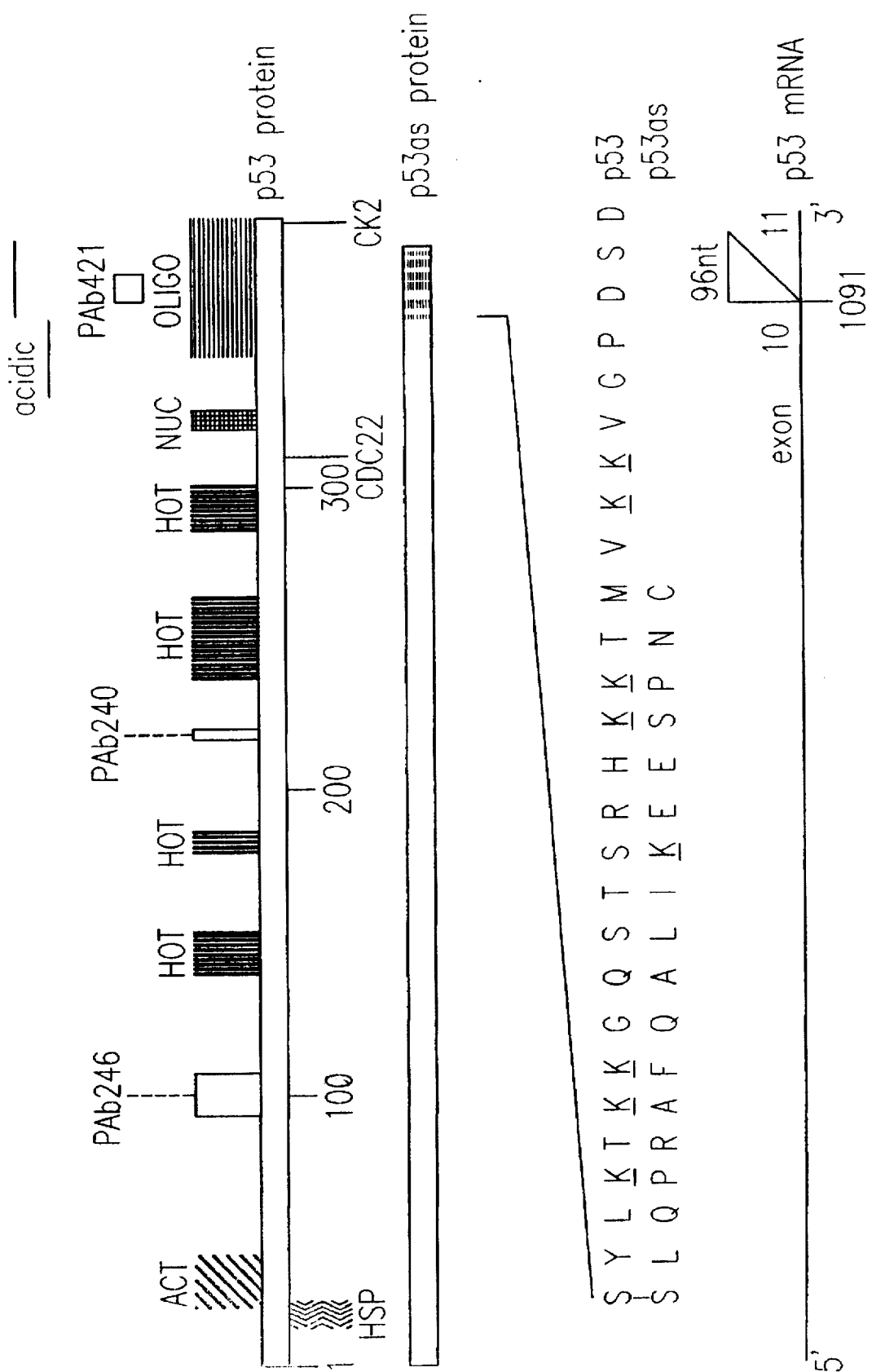
FIG. 3 is a domain map of p53 protein showing changes introduced by alternative splicing. Mouse p53 has 390 amino acids. Domains (see Vogelstein et al., (1992), "p53 function and dysfunction", Cell 70, 523–526 and references therein) are ACT: transcriptional activation domain; HSP: heat shock protein binding region of mutant p53; HOT spots; highly conserved regions among p53 proteins in which most transforming mutations occur; PAb240; region binding antibody conformation-specific for certain mutants, murine amino acids 156–214; PAb246: region binding antibody to normal wt. conformation, murine amino acids 88–109; PAb421: region binding antibody to wt. and mutant conformation, amino acids 370–378; NUC:nuclear localization signal; CDC2 kinase serine phosphorylation site; CK2 casein kinase serine phosphorylation site, which is also the site of 5.8rRNA binding; OLIGO: site of p53 self-association. The expected changes in the C-terminal region of protein translated from alternatively spliced wt. (Han et al., (b) (1992), supra) or mutant p53 mRNA (Arai et al., (1986) "Immunologically distinct p53 molecules generated by alternative splicing", *Mol. and Cell. Biol.*, 6, 3232–3239) are shown. The segment of intron 10 retained in p53as mRNA is indicated as a triangle between exons. Acidic amino acids (within a predicted alpha-helix spanning 334–356) and basic amino acids (between position 363 and 386—underlined in the C-terminal peptide sequence at bottom) are labeled according to Sturzbecher et al. (1992), "A C-terminal a-helix plus basic region motif is the major structural determinant of p53 tetramerization", *Oncogene* 7, 1513–1523.

The translation of alternatively spliced p53 results in the substitution of 17 amino acids and in truncation of the regularly spliced form of p53 by 9 amino acids (FIG. 3). The protein translated from the alternatively spliced p53 RNA lacks the serine-389 casein kinase II and RNA binding site, the epitope for PAb421 p53 antibody binding and the basic oligomerization domain, with the potential for profound effects on p53 oligomerization, DNA binding and transcriptional activation.

In spite of the evidence for alternative mRNA species from the single p53 gene, prior to the present invention, no wild type endogenous variants of p53 protein have been detected. It has now been found that the alternatively spliced wt. p53 protein (designated herein as p53as) exists in normal and tumor cells of a mouse epidermal cell transformation model and is differentially expressed during the cell cycle relative to the major p53 form. The presence of this physiological form of p53 protein in cells has important implications for normal p53 function and p53 inactivation in malignancy.

Figure 4:
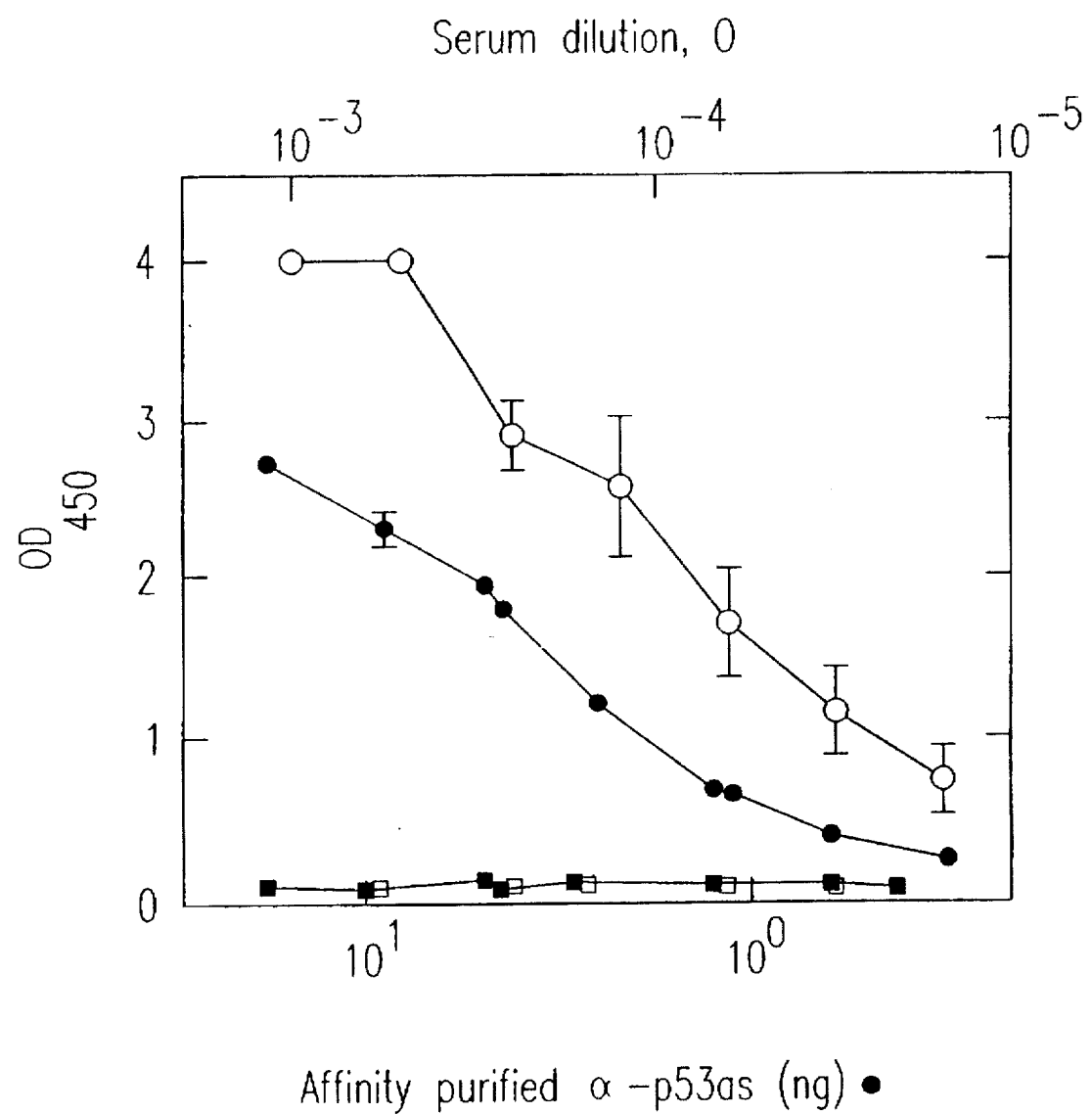
FIG. 4 shows a graph of reactivities with p53as peptide of anti-p53as serum and affinity-purified antibodies detected by ELISA. New Zealand White female rabbits were immunized with a peptide equivalent to the C-terminal 17-amino acids of p53as. p53as peptide was synthesized at the RPCI Biopolymer facility and immunizations were performed at RPCI Springville Laboratories. ELISA plates were coated with 2 µg peptide and reacted with pre-immune serum or day 63 immune serum at 1/500 through 1/640,000 (1/2 dilutions) and peroxidase-conjugated, affinity-isolated goat anti-rabbit immunoglobulin. Whole immune serum (open circles) or affinity-purified (to the peptide) anti-p53as antibodies (closed circles) were used as primary antibodies with whole pre-immune serum (open squares) or ammonium sulfate precipitated IgG fraction (closed squares) were used as controls.

In order to determine whether the p53as protein was made in cells, a polyclonal antibody to the 17 amino acid sequence unique to the mouse p53as was generated in rabbits. Rabbit serum collected at intervals after immunization was tested for reactivity to p53as peptide coated on ELISA plate wells (FIG. 4). High titer serum (shown) was affinity-purified against the 17 amino acid peptide. The reactivity (per µg antigen) of 10 ng affinity-purified antibody was approximately equivalent to a 1/40,000 dilution of whole anti-p53as antiserum. Anti-p53as reactivity in the ELISA and indirect immunofluorescence assays was blocked competitively by pre-incubation of antibody with the p53as peptide.

Immunoprecipitation

Figure 5:
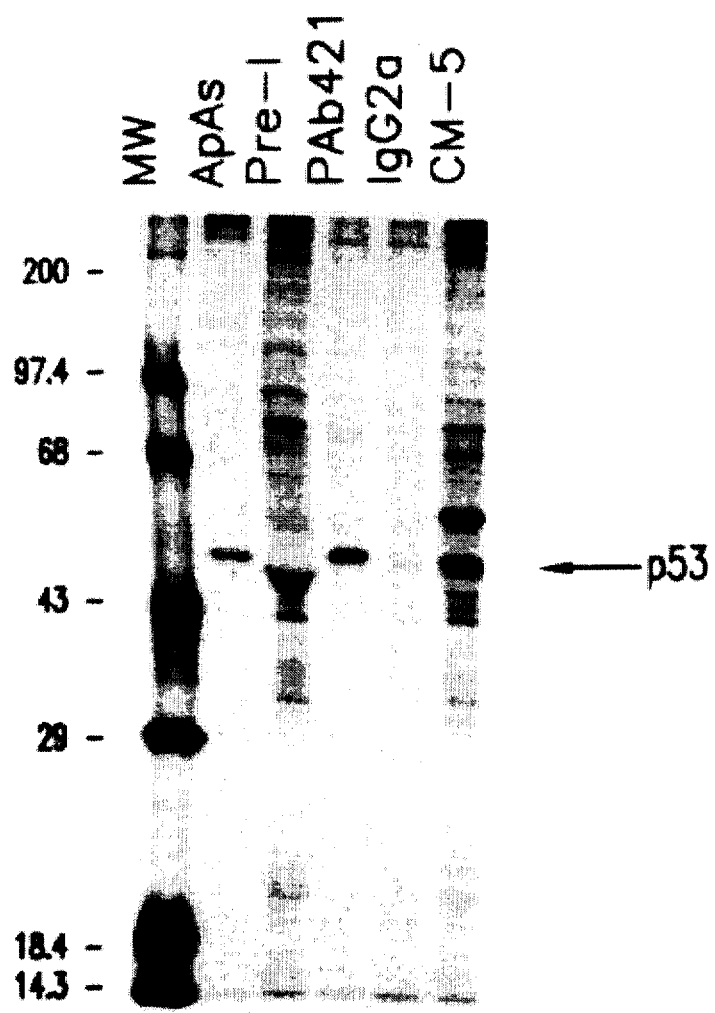
FIG. 5 shows an anti-p53as immunoprecipitation of a 53 kd protein. Immunoprecipitation of p53as from squamous cell carcinoma line 291.03RAT: $^{35}$S methionine-labeled cells were lysed and $2\times10^7$ cpm of lysate were reacted with the antibodies of antisera indicated: ApAs, affinity purified anti-p53as; Pre-I, pre-immune rabbit serum; PAb421 anti-p53 antibody to an epitope absent in p53as; IgG2a, mouse IgG idiotype control for PAb421; CM-5, rabbit polyclonal anti-p53 antibody reactive with both p53 and p53as proteins; MW, molecular weight standards (kd). After separation from the antibody complex by heating at 85° C. for 5 min., proteins were resolved by electrophoresis as described in Experimental Procedures. 53 kd proteins were detectable by PAb421 and affinity purified anti-p53as (ApAs) and rabbit polyclonal anti-p53 serum CM5.

In order to determine its reactivity with cellular proteins, affinity-purified antiserum to p53as was reacted with mouse epidermal cell lysates (FIG. 5). A 53 kd protein was immunoprecipitated by anti-p53as. This protein migrated slightly faster on 10% polyacrylamide gels than p53 protein immunoprecipitated by PAb421 (which binds to a carboxyl terminal epitope absent in p53as). Rabbit polyclonal anti-p53 antibody CM5 recognized a broader band spanning the region containing more discrete PAb421- and anti-p53as-reactive forms.

Indirect Immunofluorescence

Figure 6A:
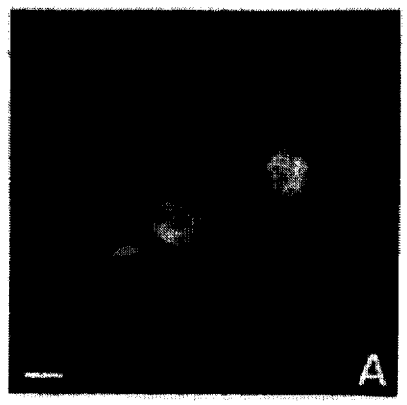
FIGS. 6A, 6B, 6C, 6D, 6E and 6F of the drawings show immunofluorescence fields indicating nuclear localization of p53as antigen activity. Cells were plated at $1.5\times10^4$ cells/cm$^2$ on glass coverslips and grown until about 70% confluent. Nuclear reactivity was detected using affinity-purified anti-ASp53 antibody in indirect immunofluorescence assays of 100% EtOH-fixed cells (A). This reactivity was completely blocked by competition with 1:1 ratio (by weight) of the 17 amino acid peptide corresponding to the C-terminus of the p53as protein (C). No competition was evident with up to a 10:1 ratio of an unrelated 16 amino acid peptide (E). Phase contrast optics corresponding to the immunofluorescence field are shown at right (B, D, F). Findings were similar for all epidermal cell lines (transfectant clone 119 of 291.03RAT is shown). Fluorescence in IgG2a, IgG1 or ammonium-sulfate fractionated pre-immune serum controls were negligable (data not shown). Bar equals 15 µm.
Figure 6B:
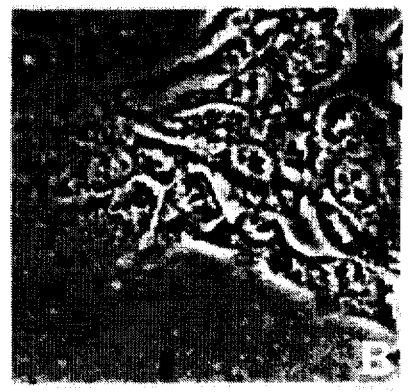
Figure 6C:
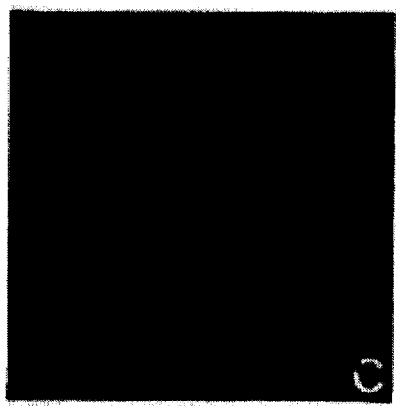
Figure 6D:
Figure 6E:
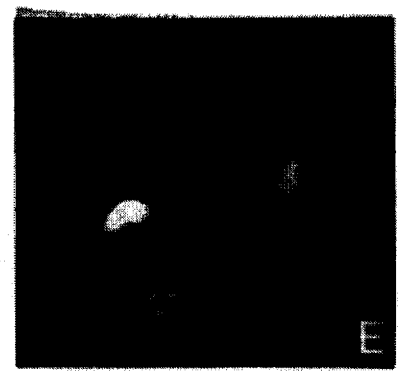
Figure 6F:

The location and incidence of expression of p53as in cell populations grown on coverslips was determined by indirect immunofluorescence. As shown in FIG. 6, nuclear staining was observed with affinity-purified anti-p53as antibody. This activity was completely blocked by competitive binding with p53as peptide (FIG. 6C). Anti-p53as antibody reactivity in 291 nontransformed cells and carcinoma cells was always nuclear under the conditions of these assays (data for clone 119 is shown), and in this respect, was like PAb246 antibody reactivity which recognizes the tumor suppressor conformation of p53. This was true even in clones of 291.03RAT transfected with the pmMTval-135 temperature sensitive mutant of p53 in which PAB421 reactivity was cytoplasmic as well as nuclear. These results suggest that, like the major p53 form, wt. p53as protein exerts its effects primarily in the nucleus.

p53 Expression in Nontransformed Cells and Tumor Cells

Figure 7:
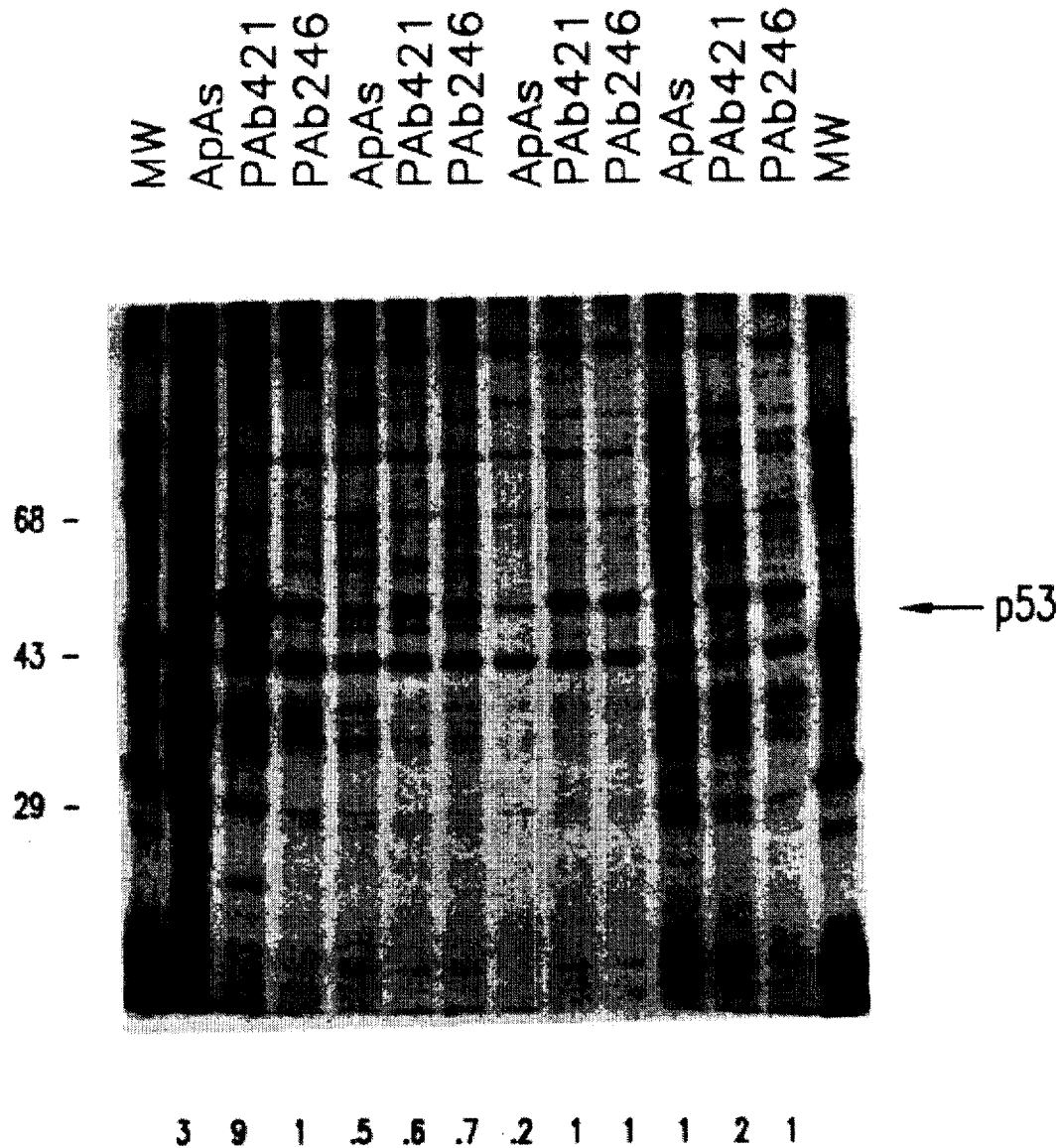
FIG. 7 shows comparative immunoprecipitation of p53 from proliferating (LC) or differentiating (HC) nontransformed parental 291 cells and from 291.03RAT (03RAT) carcinoma cells or its derivative clone 119 transfected with a mutant p53 (valine-135). Cell lysates are incubated with 2 µg PAb421, 4 µ PAb246 or 1.4 µ anti-p53as (APAS) in NET/GEL. Immunocomplexes were incubated with 5 mg protein A for 2 h at 4° C., centrifuged and immunoprecipitated protein was eluted from pellets with heating at 85° C. for 15 min. After centrifugation proteins in the supernatants were separated by electrophoresis on a 10% polyacrylamide denaturing gel with molecular weight standards (MW, kd). Immunoprecipitable p53as protein in clone 119 could have resulted from transfected mutant transcripts or from endogenous wt. p53as RNA. To assist in comparisons of a particular antibody reactivity among the cell lines, the densities of the p53 signal in each lane are provided (numbers at bottom of each lane) relative to ApAs reactivity of 291LC as 1.

Squamous cell carcinoma 291.03RAT expresses 3-fold more p53 mRNA and up to 10-fold less p53 protein (PAb421 and PAb 246 antibody reactivity) than the progenitor 291 cells (Han et al. (a) (1992), "Altered expression of wild-type p53 tumor suppressor gene during murine epithelial cell transformation", Cancer Research 52, 749–753). Comparison of the expression of p53as protein in these cell lines was done by immunoprecipitation. As shown in FIG. 7, reactivity with anti-p53as antibody was detected in nontransformed 291 cells and carcinoma cells. The p53as-precipitable protein in these cell lines migrates slightly faster than the PAb421 and PAb246-precipitable proteins, as expected from the truncation of p53as by 9 carboxy-terminus amino acids (expected to result in an approximately 1 kd difference in molecular weight). As expected from previous studies (Han et al. (a) supra) immunoreactivity to all three anti-p543 antibodies was lower in 291.03RAT carcinoma cells than normal cells. The ratio of immunoprecipitable protein in populations of proliferating cells vs. differentiating 291 cells was higher for anti-p53as (5/1) and for PAb421 (ratio of 2/1) than PAb246 reactivity (1/1). Elevated PAb421 reactivity in proliferating populations also was noted by Milner (1984), "Different forms of p53 detected by monoclonal antibodies in non-dividing and dividing lymphocytes", Nature 20, 143–145, in studies of mouse lymphocytes. The present results suggested that p53as protein might be differentially expressed relative to PAb421 and PAb246 protein, dependent upon cellular proliferative or differentiative states.

Figure 8:
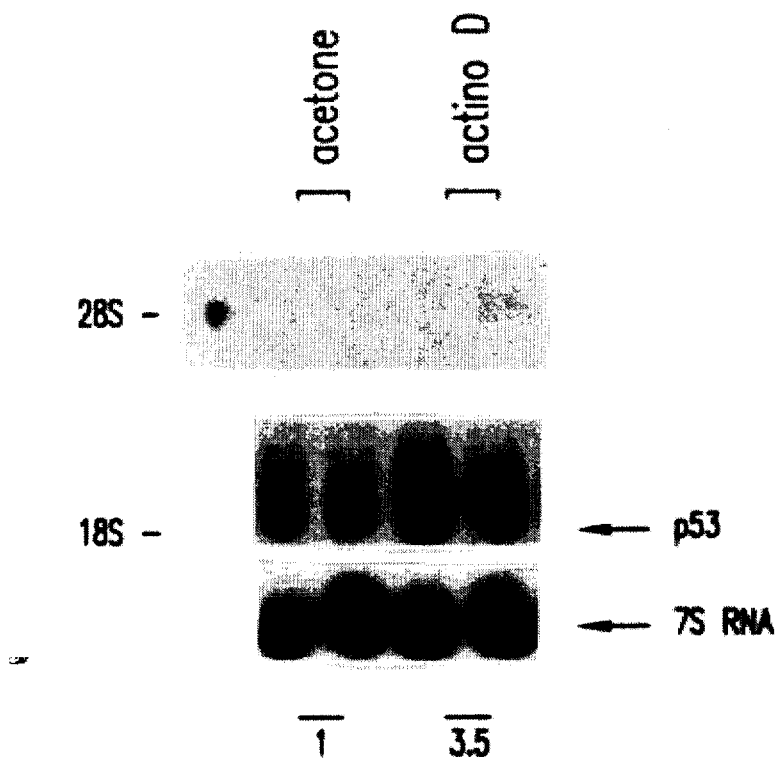
FIG. 8 shows a northern blot of p53 RNA in 291.05RAT carcinoma cells following treatment with actinomycin D. Cells were harvested after exposure to 0.5 nM actinomycin D or 0.2% acetone for 48 h and RNA was extracted as detailed in Experimental Procedures.

Response to Actinomycin D p53 protein has been postulated to participate in a cell cycle checkpoint regulating entry into S phase after exposure of cells to DNA damaging agents such as actinomycin D. Cells expressing wt. p53 (PAb421 reactivity) arrest in the G1 stage of the cell cycle following DNA damage and p53 immunoreactivity is coordinately increased. Prior to studies of the cell cycle distribution of p53as-positive epidermal cells, experiments were performed to determine whether p53as protein also may respond to DNA damage, whether it was possible thereby to maximize the percentage of p53as-positive cells in the cell population, and to compare the response of nontransformed and malignant epidermal cells. Moderately-differentiated squamous cell carcinoma line 291.05RAT was used for these studies because it expressed higher levels of immunoprecipitable p53 protein than 291.03RAT, but like 291.03RAT is derived from epidermal clone 291 and has the wt. p53 gene (Han et al. (a) supra). Treatment with actinomycin D induced p53 and p53as protein expression in two separate experiments, based on the percentage of cells positive for reactivity with p53 antibodies by indirect immunofluorescence (Table 1). The increase in positive cells was less for p53as than for PAb421 and PAb246 reactivities and required a higher concentration of actinomycin D, but this may reflect the lower abundance of p53as protein. As in untreated 291 epidermal cells and in the 291.03RAT tumor cells expressing wt. p53, the p53as antibody reactivity in actinomycin D-treated cells was nuclear. The p53as-positive nuclei were also positive for PAb421 or PAb246, whereas most PAb421(+) or PAb246(+) cells were negative for p53as antibody reactivity. The abundance of p53 RNA in actinomycin D-treated 291.05RAT cells was increased over 3-fold according to northern blot analysis (FIG. 8). In an independent cell preparation, reverse transcriptase-polymerase chain reaction (RT-PCR) was performed using primers which amplify a segment from nt 1042 to 1539 including the C-terminus coding sequences of p53 or p53as as described previously (Han et al. (b), supra). Both p53 and p53as transcripts were increased coordinately in samples from actinomycin-D treated cells compared to controls (data not shown), suggesting that the response of epidermal cells to actinomycin D involve increases in RNA abundance. The increase in abundance of p53 antibody reactivity following actinomycin D treatment was similar to the response of ML-1 and normal myeloid progenitor cells to γ-ray reported by Kastan et al. (1991), "Participation of p53 protein in the cellular response to DNA damage", *Cancer Research*, 51, 6304–6311. However, the abundance of p53 RNA was not increased in response to γ-ray and the authors suggested that the observed changes in p53 immunoreactivity resulted from a posttranscriptional mechanism. The current findings are consistent with a functional role for p53as protein along with p53 protein in cellular response to actinomycin D.

Flow Cytometry

The elevation of wt. p53 coordinated with G1 arrest of cells in response to various DNA damaging agents suggested a role as a G1/S cell cycle checkpoint permitting time for repair of DNA damage or induction of programmed cell death in severely damaged cells (Lane, (1992), p53, "Guardian of the genome", *Nature* 358, 15–16). Flow cytometry was performed in order to determine whether p53as antigen activity was differentially expressed during the cell cycle. Cells which had been exposed to actinomycin D or solvent were stained with antibodies to p53as and PAb421 or PAb246, taking advantage of the different species of origin of the polyclonal and monoclonal antibodies to permit immunodetection of p53as and p53 antigens in the same cell. Phycoerythrin (red) conjugated to anti-rabbit immunoglobulin was used to recognize p53as and FITC (green) conjugated to anti-mouse immunoglobulin was used to recognize PAb421 and PAb246. The specificity of anti-p53as is demonstrated in FIG. 9. Coordinates were set based on fluorescence intensity to divide detected events (single cells) into those positive for p53as alone (region 1, R1), positive for p53as and PAb421 or PAb246 R2), negative for p53as and positive for PAb421 or PAb246 (R3) and negative for both anti-p53as and PAb421 or PAb246 (R4). The carcinoma cells were rarely positive for anti-p53as alone (FIG. 9, R1). Cells positive for anti-p53as also were positive for PAb421 (R2, shown) or PAb246. Competition with p53as peptide, but not an unrelated peptide, completely blocked events detectable in the R2 region (shown for 291.05RAT in FIG. 9 and for 291 cells in FIG. 10), without reducing the percentage of R3 events, verifying the specificity of the anti-p53as antibody. Events from each region R1 through R4 were collected in quantity (see FIG. 9) for analysis of cell cycle distribution, represented in the histograms (FIGS. 9 and 10). The distribution of actinomycin D-treated 291.05RAT cells (shown) and control cells were essentially the same. PAb421(+)/p53as(−) 291.05RAT carcinoma cells were distributed primarily in the G0/G1 phase of the cell cycle, while p53as(+)/PAb421(+) cells were preferentially in the G2/M phase of the cycle (FIG. 7). Particularly striking is the distribution of p53as(+) cells in a "tail" indicating DNA content in excess of G2/M cells. Since single cells only were collected for analysis, such cells are likely to have undergone DNA synthesis or even mitosis, but failed to undergo cytokinesis. Inspection of p53as(+) cells grown on coverslips revealed that most (approximately 85%) contained two or more nuclei (data not shown), supporting the conclusion that these carcinoma cells continued to synthesize DNA and undergo Karyokinesis (nuclear division) but failed to undergo cell division. Nontransformed 291 cells, cultured under conditions favoring proliferation (LC), were treated similarly for comparison with carcinoma cells. As shown in FIG. 10, untreated cells were primarily in the G2/M stage. In response to actinomycin D, the distribution changed in favor of G0/G1, suggesting that both p53as protein and p53 protein reactive with PAb421 or PAb246 contribute to G1 arrest of normal cells exposed to DNA damage. In contrast to carcinoma cells, a population of 291 cells positive for anti-p53as reactivity alone was observed (FIG. 10, R1). These showed a similar cell cycle distribution to cells labeled with anti-p53as and Pab421 or Pab246. Unlike the carcinoma cells, the p53as(+) 291 cells observed on coverslips were generally mononucleated (data not shown).

The percentage distribution by cell cycle stage of nontransformed 291 and 291.05RAT carcinoma cells treated with actinomycin D or solvent controls are presented in Table 2. The preferential association of p53as antigen activity with G2/M and >G2/M, the association of p53 protein (reactive PAb421 and PAb246) with G0/G1 and the response to actinomycin D were consistent among a total of 3 independent experiments per cell type. In nontransformed 291 cells, actinomycin D increased the percentage of cells expressing immunodetectable p53as and p53 (PAb421 and PAb246) by approximately 4-fold and resulted in preferential accumulation of cells in the G1 phase of the cell cycle compared to solvent controls. In contrast, the 291.05RAT tumor cells showed little difference in the percentage of cells in G1 in response to actinomycin D treatment, suggesting that the p53 protein in these cells was less capable of causing G1 arrest, even though the percentages of cells positive for PAb421 and PAb246 were elevated.

Human p53as Peptide

Human p53as protein is defined herein as the human p53 protein 1) which is generated from a p53 transcript detectable in human cells by reverse transcriptase (RT)/polymerase chain reaction (PCR) (as described below) which is itself generated by alternative splicing of a region of intron 10 of the human p53 gene, and 2) which contains carboxyl terminal amino acids distinct from those of the major human p53 protein. (Singular is used but is not meant to rule out the possibility that more than one p53as protein is made in human cells). Antibodies to human p53as peptide permit verification of the presence of p53as in human cells.

Prior to the present invention, no human p53as protein in normal cells (alternatively spliced at the carboxyl terminus, analogous to mouse p53as) has been reported or suggested. The mouse and human p53 cDNA sequences are 81% identical and have functional domains in common. There are three lines of evidence pointing to the existence of human p53as. First, two PCR products have been amplified by RT/PCR from human cDNA using primers which span intron 10 created from mouse exon 10 and exon 11 sequences. Second, two p53 proteins are detectable by molecular weight differences in western immunoblots or immunoprecipitations using polyclonal antibodies to human p53, for example, by Gupta et al. (Proc. Natl. Acad. Sci. 90: 2817–2921, 1993) who used antibody CM-1 and protein from Hodgkins disease tumor cells. This has been attributed to either distinct phosphorylation states or a polymorphism at amino acid 72. CM-1 is expected to react with multiple regions on the p53 gene and thus would be expected to react with both human p53 and p53as proteins. Thus the presence of human p53as could account for the data in the literature demonstrating two p53 proteins distinguishable by molecular weight. Third, human intron 10 encodes a peptide which has a motif (SPPC) similar to the last 4 amino acids of the mouse p53as (SPNC).

The peptide unique to human p53as is identified as follows:

Primers are constructed which are used to amplify by polymerase chain reaction (PCR) a region of the human p53 cDNA including part of exon 10, all of intron 10 sequences retained in the alternatively spliced p53 mRNA and part of exon 11. Human cDNA is generated from cellular RNA (isolated by guanidinium/cesium chloride extraction) by RT/PCR. RT/PCR is carried out as follows: 5 µg of human cell total RNA is combined with 1 mM each of 4 deoxynucleotidetriphosphates, 5 µg random hexamer primer (to make cDNA to all available mRNA), 5 µAMV reverse transcriptase (RT, 5 to 10 units per µl), 3.5 mM MgCl$_2$ (or as optimized), 2.5 µl RNasin 5 µl PCR buffer (Perkin Elmer; without Mg$^{2+}$) and depc-treated water to adjust the volume to 50 µl. Reaction is allowed to proceed at 23° C. for 10 minutes, 42° C. for 1h and 95° C. for 10 minutes then transferred to ice. An additional 0.2 µl of RT is added and the reaction is repeated 1X. 1 µl of the RT reaction product mix is used to provide the cDNA templates for human p53 and p53as C-terminal regions for amplification by PCR. PCR is optimized to obtain efficient production of the specific product and minimize background. PCR is performed for 35 cycles of denaturation (95° C., 30 sec), annealing (60° C., 1min) and extension (72° C, 3 min) in a DNA thermal cycler. Amplified fragments of human p53 and p53as C-terminal coding regions are desalted by centricon ultrafiltration, digested with the restriction enzymes appropriate to the synthetic primers (see example below) and isolated from low melting temperature agarose for cloning into pGEM3zf (+) (Promega) for the sense strand or pBluescript KS(+) (Stratagene) for the antisense strand and transfected into *E. coli* for production and sequencing as we have described (Han et al. supra). Human cells as the source of RNA include (but are not limited to) normal human epidermal keratinocytes and two clones (B and F2A) of squamous cell carcinoma line SCC-12. The PCR amplification product generated using the primers which span intron 10 include the major p53 transcript and p53as transcript(s). These are distinguished by differences in molecular weight and/or by sequencing of the amplified PCR products as has been demonstrated previously for mouse p53as transcripts (Han et al. (b) supra). Sequencing of the PCR products permits determination of the sequence of the protein encoded by human p53as RNA. The amino acid sequence of the human p53as protein is compared to that of the major human p53 protein to determine the unique sequence at the carboxyl terminal region of human p53as protein.

An example of a primer set which spans intron 10 of the human p53 gene is: 5' primer/sense strand ATCGAAGCTTGAGATGTTCCGAGAGAGCTGAAT (within exon 10 beginning at nucleotide 17,593 of the genomic p53 sequence Genbank accession No. X54156, with additional nucleotides added to the 5' end, ATCG and restriction endonuclease site HindIII to facilitate cloning and sequencing—underlined) and 3' primer antisense strand ATCGTCTAGAGCTTCTGACGCACACCTATTG (within exon 11 beginning at nucleotide 18794 in the 5' to 3' direction to nucleotide 18774, with ATCG and XbaI restriction endonuclease site added—underlined).

Polyclonal Antibody Specific for Mouse p53as Protein

Polyclonal antibody to mouse p53as unique peptide noted above has been raised in rabbits, its high titer has been determined by enzyme linked immunosorbent assay (ELISA), its specificity for p53 protein has been determined by immunoprecipitation from mouse cells, western immunoblotting of anti-p53 precipitable protein to a polyclonal antibody to p53 (CM5, reactive with epitopes shared by p53 and p53as proteins), ability of the peptide to competitively block reactivity in cells and in western immunoblots, and the ability of the p53as peptide to block binding of p53as antibody but not block the binding other p53 antibodies (PAb421 and pAb246) which bind to epitopes distinct from the unique region of p53as.

The polyclonal anti-peptide antibody is produced in rabbits as described in General Procedures below.

Monoclonal Antibody Specific for Mouse p53as Protein

Hybridoma cell lines have been produced by fusion of spleen cells from BALBc mice immunized with mouse p53as peptide. The procedure is found in General Procedures below.

The monoclonal antibodies from each hybridoma cell line producing specific antibody as determined by ELISA is to be tested for reactivity with mouse cellular p53as by immunoprecipitation, western immunoblotting and immunofluorescence as described for polyclonal antibody to mouse p53as above. Specificity is determined by competition with mouse p53as peptide. Such a hybridoma cell line has been deposited with ATCC, Rockville, Md. having ATCC accession number HB 11685.

Polyclonal Antibody Specific for Human p53as Protein

The peptide unique to human p53as, determined as described above, will be synthesized and used to immunize rabbits following the procedures used to generate polyclonal antibody to mouse p53as, described in the manuscript provided and in General Procedures. An example of such a peptide selected based upon similarities with mouse p53as unique peptide is the following 20 amino acid peptide encoded by human intron 10 sequences: REKGHRPSHSCDVISPPCFC.

Monoclonal Antibody Specific for Human p53as Protein

The peptide unique to human p53as, determined as described above, will be synthesized and used to immunize mice following the procedures used for polyclonal antibody to mouse p53as described above and in General Procedures below.

Note that the species specificity of each antibody will be determined; that is, for example, testing of whether an antibody generated to mouse p53as peptide also binds human p53as and whether antibody to human p53as binds mouse p53as protein will be performed.

General Procedures for Immunizing Mice with Synthetic p53as Peptides (Mouse or Human)- Monoclonal Antibody Production The procedures to be used are based on standard procedures for generating monoclonal antibodies.

The p53as peptide of mouse or human origin is stored protected from light and oxygen until use. It is reconstituted just prior to injection. Unmodified peptide is used as immunogen initially because this was successful in the generation of polyclonal antibodies to mouse p53as protein. Alternatives which will be used if necessary to improve immunization include conjugation to another protein (for example, ovalbumin)), or use of full length p53as protein generated in insect cells using a baculovirus vector system. Such vectors containing p53as cDNA have already been made in this laboratory for production of mouse p53as protein.

For each mouse, 250 μl (30 to 50 μg of peptide) is emulsified with an equal volume of Freund's complete adjuvant.

The emulsion is injected into BALB/c female mice (weighing approximately 20 g each) intradermally at multiple sites along the dorsum and intraperitoneally. (If necessary to improve the immunization response, an alternative mouse strain will be used.)

Four weeks later, boosting of the mice with an intraperitoneal injection of 100 μl (20 μg peptide) mixed with Freund's incomplete adjuvant is performed.

Two weeks later, serum is tested for antibody titer by ELISA as per manuscript provided.

Three days before the fusion, the best responder is reboosted with an intravenous injection of 100 μl (20 μg peptide) without adjuvant.

Cell Fusion

Preparing Myeloma Cells for Fusions

Myeloma cells are thawed from liquid nitrogen and placed in culture one week prior to the fusion. The cells are grown in order to reach a cell density of $5 \times 10^5$ cells/ml one day before the fusion. On the morning of the fusion, 10 ml of cultured cells are diluted with an equal volume of CMEM.

| Complete Media Preparation (CMEM): | |
|---|---|
| 0.5 ml | gentamicin sulfate |
| 5.0 ml | Pyruvic acid stock solution |
| 5.0 ml | Hypoxanthine stock solution |
| 5.0 ml | Thymidine stock solution |
| 5.0 ml | Oxaloacetate stock solution |
| 5.0 ml | Penicillin G stock solution |
| 5.0 ml | Bovine insulin stock solution |
| 50 ml | NCTC 109 (MA Bioproducts) |
| 100 ml | Fetal Bovine Serum (heat inactivated) |

The above solutions are added to a sterile 500 ml bottle and volume is adjusted to 500 ml with Dulbecco's MEM (with L-glutamine, with D-Glucose at 4500 mg/L, without Sodium Pyruvate, Gibco). The medium is sterilized by 0.2 micron filtration and tested for contamination by incubate overnight at 37° C. CMEM is stored at 4° C. and used within 2 weeks.

Preparing Splenocytes for Fusions

The mouse is sacrificed and the spleen is aseptically removed. Contaminating tissues are dissected and discarded.

The spleen is ground on a stainless steel mesh to release the cells.

The splenocytes are washed twice with 10 ml of medium without serum and the cells counted.

Cell Fusion

Myeloma cells are washed once and resuspended in medium without serum.

The myeloma cells and splenocytes (1:10) are combined in medium without serum. These cells are centrifuged together at 800 g for 5 min.

The supernatant is removed. 50% PEG 1500 is added to the cell pellet slowly over 1 min while resuspending the cells by stirring with the end of the pipet. Stirring is continued for an additional minute. Then 1 ml medium without serum is added to the cell suspension over the next minute. Finally, 9 ml medium is added over 2 min with stirring. The cells are centrifuged at 400 g for 5 min.

The supernatant is removed and the cells resuspended in 30 ml HAT media.

HAT Media Preparation:

HAT medium is prepared the same as CMEM but 1.0 ml aminopterin stock solution and 1.0 ml glycine stock solution are added before bringing media to a total volume of 100 ml.

100 ml of cells are dispensed into the wells of 96-well plates. The plates are incubated in a 5% $CO_2$ atmosphere.

Single-cell cloning

Screening Positive Clones by ELISA.

About 50 μl of culture supernatant are placed in the wells of another 96-well microtiter plate that has been coated with p53as synthetic peptide appropriate to the antibody (mouse or human p53as peptide). Positive clones are detected by ELISA as presented in the manuscript attached.

Preserving Positive Clones.

After a positive well has been identified, the cells are transferred from the 96-well plate to the well of 24-well plate containing the same medium. After the 24-well plate culture becomes dense, it is transferred to 100-mm dish. Freeze the cells at the 100-mm dish stage.

Limiting Dilution

On the day before cloning, a spleen cell suspension is prepared according to the procedure described in the fusion technique above. $10^3$ spleen cells per well are plated into a 96-well plate (using one drop per well). A minimum of $10^5$ proliferative hybridoma cells from a 25 cm$^2$ flask are used for cloning.

The hybridoma cells are subcultured 24–48 hours before cloning by diluting an actively growing culture 1:1 with fresh media. Cells in mid-log phase are used for the limiting dilution.

Cell number is adjusted to $10^5$ viable cells per ml (cell viability of >70%).

Serial 10-fold dilutions are made (e.g. $10^4$, $10^3$ per ml.)

In a 50 ml tube, 0.30 ml of the $10^3$ hybridoma cells is added per ml and 29.7 ml of CMEM.

One drop from a 2.0 ml (50 μl) pipette of the cell suspension is added to each well of the 96 well plates with the spleen cells prepared the day before cloning.

Cultures are observed every 2 to 3 days and wells with a single cell clone are marked.

Clones are assayed for anti-p53as activity by ELISA when they cover 25% of the well. Positive clones are transferred to 24 well plates, to 100-mm dishes, then hybridoma cells are cryopreserved in Nunc cryotubes.

Ascites Production 8 week old BALB/c mice are injected with 0.4 ml of pristane intraperitoneally.

After two weeks, 0.5 ml cells ($10^5$ cells) in mid-log phase are injected into each pristane-treated mouse.

After 2–3 weeks, the mice are sacrificed and the ascitic fluid harvested.

Ascites is centrifuged at 1000 g for 10 min, the middle layer is collected and kept at −20° C.

Monoclonal antibodies are tested by ELISA, indirect immunofluorescence, immunoprecipitation and western immunoblotting for specificity to p53as in appropriate cells (mouse or human). Ability of the antibody reactivity to be competitively blocked by the peptide used to generate it is tested.

General Procedures for Immunizing Rabbits with Synthetic p53as Peptides (Mouse or Human)- Polyclonal Antibody Production The procedures to be used are based on standard procedures for generating polyclonal antibodies.

The p53as peptide of mouse or human origin is stored protected from light and oxygen until use. It is reconstituted just prior to injection. As noted above for monoclonal antibody production, unmodified peptide is used as immunogen initially but, if necessary, conjugation to another protein will be done or full length p53as protein will be used. New Zealand white female rabbits (6–8 lb.) (4) are used for immunizations.

Procedure

Basal (pre-immune) serum is collected 1 wk. before immunization.

(day 0) 500 µg peptide per rabbit is freshly dissolved in phosphate buffered saline (PBS) & mixed with Freund's complete adjuvant (total vol. 2 ml or less) and used as antigen. Immunization is by intradermal injection at multiple sites (at least 10 sites) along the dorsum and concurrent intramuscular injection of Pertussis vaccine.

(day 21) 250 µg peptide/rabbit is freshly dissolved in PBS & mixed with Freund's incomplete adjuvant (tot. vol. 1 ml or less). Injections are intradermal on the back (at least 10 sites).

(day 28) bleed for serum. Test anti-p53as antibody titers by ELISA.

(day 35) Immunization with 250 µg peptide/rabbit as day 21.

(day 42) Test bleed for serum (day 49) Immunization with 250 µg peptide/rabbit as day 21&35

(day 56, day 63) Bleed for serum (day 77) Immunization with 250 µg peptide/rabbit as above.

(day 84) Bleed for serum on the following weekly schedule: rest, boost as necessary to maintain antibody titer (250 µg peptide/rabbit) bleed each week for 3 weeks, rest 1 week, repeat with boosting as necessary to maintain titer.

Affinity Purification of Antibody

Polyclonal antibody is affinity purified by complexing with the appropriate peptide (human or mouse p53as) coupled to an AminoLink column (see manuscript provided) through amino groups or a column in which peptide is bound through cysteine. Approximately 7 mg of peptide is required for binding to the column and antibody from approximately 25 ml of serum is purified per run. The column is reconstituted according to manufacturer's directions and reused. Affinity purified antibody is tested by ELISA, indirect immunofluorescence, immunoprecipitation and western immunoblotting for specificity to p53as. Ability of the antibody reactivity to be competitively blocked by the peptide used to generate it is tested.

As evidenced above, p53as, a physiological variant of the tumor suppressor protein p53, has been detected in mammalian epidermal cells containing the wt. p53 gene. The fact that endogenous wild type p53as protein has not been detected in cells before may be due to a number of factors including the previous failure to recognize its possible existence, its low abundance and lack of reactivity with anti-p53 monoclonal antibody PAb421. It was previously shown that the wt. p53as mRNA is present in normal mouse tissues and in cultured mouse fibroblasts at 25 to 33% of the major p53 RNA form (Han et al., (b)). Alternatively spliced p53 RNA in transformed and normal cells of different tissue types, Nucleic Acids Res., 20(8), 1979–1981. In accordance with the present invention, it has been demonstrated that the p53as protein exists in cells, that it is nuclear in location in normal epidermal and carcinoma cells, is differentially expressed in proliferating compared to differentiating normal cells and is inducible along with PAb421-and PAb246-reactive p53 by the DNA damaging agent actinomycin D.

The presence of cells with greater than the G2/M content in acetone controls suggests that these are a physiological component of the epidermal cell populations. The higher ratio of p53as to other p53 antibody reactivities in cells cultured under LC conditions suggests that p53as is preferentially expressed in proliferating populations. Yet, the distribution of p53as-positive cells in G2/M and >G2/M appears more likely to reflect a growth arrest or maturation pathway. Epidermal cell populations are composed of proliferating and differentiating or growth-arrested cells, reflecting the balance of growth and differentiation strictly maintained in epidermis. Even under conditions favoring proliferation (LC conditions, see Experimental Procedures) basal (proliferation-associated) cell markers are lost with time after plating and differentiating cells increase as a percentage of the total population (Kulesz-Martin et al., (1989), "Pemphigoid, pemphigus and desmoplakin as antigenic markers of differentiation in normal and tumorigenic mouse keratinocyte lines",Cell Tissue Kinet, 22, 279–290. Mouse keratinocytes exhibit a bimodal DNA content, containing stable populations near diploid and near tetraploid 3 to 19 days after establishment in primary culture (Kulesz-Martin et al. (1983), "Properties of carcinogen altered mouse epidermal cells resistant to calcium-induced terminal differentiation", Carcinogen, 4, 1367–1377). While the 291 cells are sub-tetraploid (Kulesz-Martin et al., (1985) "Mouse cell clones for improved quantitation of carcinogen-induced altered differentiation", "Carcinogenesis" 6, 1245–1254) they appear to retain the capacity to generate a subpopulation of cells with doubled DNA content. Davies et al. (1993), "Antioxidants can delay liver cell maturation which in turn affects γ-glutamyltranspeptidase expression", Carcinogen, 14, 47–52, have discussed the changes in ploidy from 2N to 4N and 8N which occur by mitosis without cytokinesis and accompany maturation of normal liver cells. They note that after partial hepatectomy, regenerating liver contains increased numbers of cycling cells and binucleated tetraploid cells which undergo DNA synthesis and amitotic cytokinesis, resulting in mononucleated tetraploid cells. The presence of cells with >G2/M DNA content in populations of epidermal cells could reflect progress along a maturation pathway. The increase in percentage of p53as(+) 291 non-transformed cells in response to actinomycin D suggests that p53as protein cooperates with p53 detectable by PAb421 and PAb246 in the DNA damage induced G1 arrest. However, the preferential association of p53as protein immunoreactivity with G2/M occurs in control and in actinomycin D-treated cells, suggesting that it reflects a physiological activity of p53as protein in the G2 state rather than a consequence of treatment. It is intriguing that actinomycin D and γ-ray treatment induces G1 and G2 arrest, but only G1 arrest was associated with a rise in PAb421 activity (Kastan et al., supra). One could speculate that p53as protein has a role in G2/M arrest in response to DNA damage. In contrast, regardless of increased percentage of p53-positive cells, no actinomycin D-dependent changes in cell cycle distribution occurred in carcinoma cells, suggesting that carcinoma cells are defective in the ability to undergo cell cycle arrest.

Additional inferences about the functional properties of p53as protein can be made based on the studies of others.

Changes at the carboxyl terminus of p53 protein engineered by site-directed mutagenesis or deletion mapping have been shown to have dramatic effects on p53 structure and function (Hupp et al., supra; see FIG. 1). Sturzbecher et al., supra, demonstrated that loss of C-terminal basic residues permitted dimer formation of p53 protein but not tetramers, while Hainaut et al. (1992), "Interaction of heat-shock protein 70 with p53 translated in vitro evidence for interaction with dimeric p53 and for a role in the regulation of p53 conformation", *EMBO J.* 11, 3513–3520) showed that deletion of 25 C-terminal amino acids of p53, similarly, resulted in dimers but not higher order complexes. Since p53 protein is thought to bind to DNA as a tetramer (Bargonetti et al., (1992), "Site-specific binding of wild-type p53 to cellular DNA is inhibited by SV40 T antigen and mutant p53 ", *Genes & Dev.* 6, 1886–1898; and Stenger et al., (1992), "Formation of stable p53 homotetramers and multiples of tetramers", *Mol. Carcinogen*", 5, 102–106), restriction of p53as to dimer formation may influence its interactions with DNA, see FIG. 2.

Properties of the mutated form of alternatively spliced p53 protein translated in vitro from the M-8 cDNA clone (Arai et al., supra) have been reported. Hainaut et al. supra, observed that, following in vitro translation, the mutant alternatively spliced p53 protein encoded by M-8 formed monomers and dimers, but not tetramers. Like the mutant M-8 protein, wt. p53as has lost the basic amino acids of the C-terminus but retains the acidic amino acids shown to permit dimer formation. These results support the idea that wt. p53as may have distinct properties from the major p53 protein form. However, the M-8 p53 cDNA sequence has a nucleotide substitution at nt 395 resulting in a change from cysteine-132 to phenylalanine. Eliyahu et al. (1990), "Meth a fibrosarcoma cells express two transforming mutant p53 species", *Oncogene* 3, 313–321), reported that plasmids containing the M-8 p53 cDNA had transforming activity in transfected cells. Mutations within this region of p53 without alternative splicing are defective in tumor suppressor function and DNA binding (Eliyahu et al., supra; Finlay et al., (1989) "The p53 proto-oncogene can act as a suppressor of transformation", *Cell*, 57, 1083–1093; and Vogelstein et al., (1992), supra. Thus the M-8 protein has a mutation which affects its function apart from the C-terminal changes due to alternative splicing. p53 protein translated from cDNA clone M-8 does not react with PAb248 antibody (which, like PAb246 is wt. conformation-specific) or, due to loss of the C-terminal epitope, PAb421 (Wolf et al., (1985) supra). Since the wt. p53as has a distinct conformation compared to the mutated M-8 protein, functional properties such as DNA binding cannot be predicted from studies of M-8 protein and must be tested directly.

In addition to alterations in the oligomerization domain predicted from the above studies, p53as has lost the casein kinase II phosphorylation/5.8s rRNA binding site located at serine 389 (see FIG. 1). Loss of the phosphorylation site at serine-389 by mutation negates p53 anti-proliferative activity (Milne et al., (1992), "Mutation of the casein kinase II phosphorylation site abolishes the anti-proliferative activity of p53 ", *Nucleic Acids Res.* 20, 5565–5570; Bischoff et al., (1992), "Human p53 inhibits growth in Schizosaccharomyces pombe", *Mol. and Cell. Biol.* 12, 405–411; Nigro et al., (1992), "Human p53 and CDC2Hs genes combine to inhibit the proliferation of Saccharomyces cerevisiae", *Mol. and Cell. Biol.* 12, 1357–1365). Hupp et al., supra, have shown that factors acting at the C-terminus are important for activation of the DNA binding capacity of wt. p53, including: phosphorylation at the conserved C-terminal serine, PAb421 antibody binding to its carboxyl terminal epitope, and proteolysis or engineered loss of the last 30 carboxyl terminal amino acids. In addition, regions of the p53 protein which mediate binding to other cellular proteins such as heat shock protein (Hainaut et al., supra) or mdm2 (Momand et al. (1992), "The mdm-2 oncogene product forms a complex with the p53 protein and inhibits p53 -mediated transactivation", *Cell* 69, 1237–1245), conceivably could be directly or indirectly altered.

The differential expression of p53 and p53as protein immunoreactivities during the cell cycle suggest that each has a distinct function. Perhaps p53 may prove to be within the class of transcription factors which generate two functionally distinct proteins by alternative splicing (Foulkes et al., (1992), "More is better: activators and repressors from the same gene", *Cell* 68, 411–414). For example, in the case of mTFE3 factor (which regulates immunoglobulin transcription by binding to promoter and enhancer regions), there is a longer and a shorter protein form. In the shorter form amino acids predicted to form an amphipathic helix are absent and transcriptional activation activity is affected. The ability of such factors to heterodimerize amplifies the possibilities for regulation of expression of target genes.

It will be important to determine the activity of wt. p53as in tumor suppression. While originally thought to be an oncogene because initial clones of p53 harbored mutations, cloning of wt. p53 lead to the recognition of its role as a tumor suppressor gene (Finlay et al., supra; and Eliyahu et al., supra). The capacity of mutant p53 protein to drive wt. p53 into the mutant conformation uncovered its potential as a dominant negative transforming gene (Milner, 1984, supra.; and Milner et al., (a) (1991), "Cotranslation of activated mutant p53 with wild type drives the wild-type p53 protein into the mutant conformation", *Cell* 65, 765–774). Yet mutant p53 itself has transforming activity in cells which have no wt. p53, suggesting direct activities of p53 in the regulation of proliferation (Wolf et al., (1984), "Reconstitution of p53 expression in a nonproducer Ab-MuLV-transformed cell line by transfection of a functional p53 gene", *Cell* 38, 119–126). Milner (b) (1991), "The role of p53 in the normal control of cell proliferation", *Current Opinion in Cell Biology* 3, 282–286, has proposed that p53 has positive and negative functions in cell cycle regulation, dependent upon p53 conformation. One could speculate that positive or negative functions of p53 in regulation of cell cycle progression or induction of apoptosis may reside in the relative expression of different physiological variants of p53 generated by alternative splicing. Studies to compare differential functional activity of the wt. p53 and p53as in DNA binding, transcriptional activation, cellular transformation, cell cycle arrest and apoptosis will be necessary to test these possibilities.

Experimental Procedures

Cells

The strain 291 was derived from neonatal BALB/cROS mouse epidermis (West Seneca Laboratory, Roswell Park Cancer Institute) and is "normal" with respect to differentiation and morphology in vitro and in vivo (Kulesz-Martin et al. (1985) supra.; Kulesz-Martin et al. (1991), "Tumor progression of murine epidermal cells after treatment *in vitro* with 12-0-tetradecanoylphorbol-13-acetate or retinoic acid", *Cancer Research* 51, 4701–4706; Schneider et al., (1993), "7,12-dimethylbenz [∝]anthracene-induced mouse keratinocyte transformation without Harvey ras protooncogene mutations", *J. Invest. Dermatology, in press*). The cells were grown in Eagle's minimum essential medium with Earle's salts without CaCl$_2$ (GIBCO, Grand Island, N.Y.), supplemented with 5% (v/v) fetal calf serum treated with chelex-100 resin (Bio-Rad, Rockville Center, N.Y.) to reduce CA$^{2+}$ concentration, non-essential amino acids, 10% (v/v) mouse dermal fibroblast conditioned medium, 10 ng/ml EGF (UBI, Lake Placid, N.Y.), 1% (v/v) antibiotic-antimycotic (100 U/ml Penicillin, 100 µml Streptomycin sulfate and 0.25 µg/ml Amphotericin B Solution, GIBCO, Grand Island, N.Y.) and 0.02–0.04 mM Ca$^{2+}$ (designated as LC). Tumor cell derivatives of 291 (291.03RAT and 291.05RAT) were isolated from squamous cell carcinomas following exposure of 291 cells to 7,12-dimethylbenz [∝]anthracenein vitro as described (Kulesz-Martin et al., (1986), "Retinoic acid enhancement of an early step in the transformation of mouse epidermal cells In Vitro", Carcinogenesis 7, 1425–1429; Kulesz-Martin et al., (1991) supra; Kulesz-Martin et al., (1983) supra. Tumor cells were grown in minimum essential medium as above except without conditioning or EGF and with native fetal calf serum and 1.4 mM Ca$^{2+}$ (designated as HC). Clone 119 was derived by transfection of carcinoma 291.03RAT with a plasmid containing a genomic clone of mutant p53 (pmMTval135-23), obtained from Dr. Moshe Oren. It expresses predominantly wt. p53 conformation at 37° C. (unpublished results).

Antibodies

Mouse monoclonal antibodies to p53 were PAb421, PAb240 and PAb246 (Oncogene Science, Uniondale, N.Y.). Isotype IgG$_{2a}$ (PAb421 and PAb240) and IgG$_1$ (PAb246, Becton/Dickinson, Mountain View, Calif.) were used as sera controls. Rabbit polyclonal antibody CM5 was a gift from Dr. David Lane. Anti-peptide antibody to the terminal 17 amino acids unique to p53as (see FIG. 1B) was generated as follows: The 17 amino acid peptide to p53as was synthesized by the RPCI Biopolymer Facility and determined to be 90 to 95% pure by HPLC and mass spectroscopy and accurate by amino acid sequencing. Following collection of pre-immune serum, New Zealand White female rabbits were immunized by intradermal injection of 500 µg peptide plus Freund's complete adjuvant (FCA) at multiple sites, concurrent with intramuscular injection of Pertussis vaccine (RPCI Springville Laboratories). After 3 weeks, an additional 250 µg of peptide was administered with Freund's incomplete adjuvant (FIA) at weekly intervals for 3 weeks. The p53as anti-peptide serum was affinity-purified by coupling 4.4 mg p53as peptide to an AminoLink column (Pierce, Rockford, Ill.) according to manufacturers instructions. Ammonium sulfate (40%)-precipitated pre-immune serum was used as a control. Competition assays were performed by incubation of antibodies (1:1 ration by weight) with p53as peptide (sequence shown in FIG. 1) or an unrelated peptide (sequence: GRNDCIIDKIRRKNCD) for 2 h at room temperature prior to the immunoreaction with cells or peptide in ELISA assays.

Enzyme-linked Immunosorbent Assay (ELISA)

Nunc-Immuno MaxiSorb 96 well plates (Nunc, Denmark) were coated with 50 ng/well p53as peptide in 15 mM sodium carbonate buffer, pH 9.6. After blocking with 2% BSA (KPL, Gaithersburg, Md.) in PBS at 37° C. for 1 h, anti-p53 monoclonal antibodies, anti-p53as antibody (affinity-purified to peptide) or pre-immune serum control (pre-I) were diluted 1/50 to 1/640,000 and added to the wells in 100 µ volume. Secondary antibody was peroxidase-conjugated goat anti-rabbit immunoglobulin (DAKO, Carpinteria, Calif.) at 1/1000. TMB peroxidase substrate system solution (KPL, Gaithersburg, Md.) was added and color development was terminated after 4 minutes using 4M H$_2$SO$_4$. Absorbance at 450 nm was detected using a BioTek plate reader (Winooski, Vt.).

Immunofluorescence

Cells were permeabilized with 100% cold EtOH, rehydrated in PAB (PBS+0.1% Na-azide+0.5% BSA)+0.05% Tween 20 for 10 minutes, blocked with 5% normal goat serum (Vector Labs, Burlingame, Calif.) and then exposed to 10 µg/ml each of monoclonal anti-p53 antibodies PAb 421, 240 or 246 or control isotype sera IgG$_{2a}$ or IgG$_1$ overnight at 4° C. Secondary antibody for monoclonal antibodies was a 1/300 dilution of fluorescein isothiocyanate (FITC)-conjugated goat anti-mouse immunoglobulin (FisherBiotech, Pittsburgh, Pa.). Affinity purified rabbit polyclonal anti-p53as or ammonium sulfate-fractionated pre-immune serum as control was used at 7 µg/ml followed by 1/300 Texas Red-conjugated goat anti-rabbit immunoglobulin (oncogene Science). FluorSave aqueous mountant (Calbiochem, La Jolla, Calif.) was used to attach coverslips to slides. The fluorescence was viewed using a Nikon Labophot microscope equipped with epi-illuminescence. Photomicrographs were taken the a Nikon UFX-IIA automatic camera system.

Immunoprecipitation

Preconfluent cultured cells (approximately 5–10×10$^6$ cells/100mm petri dish) were incubated with 200 µCi of L-[$^{35}$S]methionine (1120 Ci/mmol) for 4 h at 37° C. in methionine-free minimum essential medium containing 2% (v/v) dialyzed calf serum. Labeled cells were lysed in buffer containing 1% (v/v) nonidet P-40, 150 mM NaCl, 50 mM Tris pH 8, 1 mM phenylmethylsulfonyl fluoride for 30 minutes at 4° C. and centrifuged at 10,000×g for 10 minutes. The supernatant was precleared with formalin-fixed Staphylococcus aureus cells (Immunoprecipitin, BRL, Gaithersburg, Md.) or with protein A-Sepharose (Pharmacia, Piscataway, N.J.). Lysate volumes corresponding to equal amount of radioactivity (2 ×10$^7$ cpm) were incubated in NET/Gel buffer (150 mM NaCl, 5 mM EDTA, 50 mM Tris pH 7.4, 0.05% NP-40, 0.025 NaN$_3$ and 0.25% gelatin) for 16 h at 4° C. with antibodies to murine p53 or isotype or serum controls. Immune complexes were precipitated with Immunoprecipitin or 5 mg of protein-A SepharoseCL-4B (Pharmacia) for 2 h at 4° C., centrifuged at 10,000×g for 10 minutes. The pellets were washed with NET/Gel buffer and eluted in loading buffer (2% (w/v) SDS, 10% (v/v) glycerol, 125 mM Tris-Cl, pH 6.8, 0.001% (w/v) bromophenol blue) by heating at 85° C. for 5 to 15 minutes and centrifugation at 10,000×g for 10 minutes. Supernatants were loaded on a denaturing polyacrylamide gel composed of 4% stacking gel (125 mM Tris-Cl, pH 6.8, 0.1% (w/v) SDS) and 10% separating gel (375 mM Tris-Cl, pH 8.8, 0.1% (w/v) SDS), and subjected to electrophoresis at 35 mA in running buffer (125 mM Tris-Cl, pH 8.3, 192 mM glycine, 0.1% (w/v) SDS). Gels were fixed in 7.5% (v/v) acetic acid/25% (v/v) methanol, soaked in enhancer solution (NEN, Boston, Mass.) and dried prior to exposure to XAR film (Kodak, Rochester, N.Y.) at −80° C. with intensifying screens.

Treatment with Actinomycin D

Cells on coverslips were treated with 0.25 nM or 0.5 nM actinomycin D (Sigma, St. Louis, Mo.) or 0.2% acetone for 48 h, beginning 24 h after plating and stained by indirect immunofluorescence as described above. For flow cytometry or isolation of cellular RNA, approximately 2 to 4×10$^6$ cells/cm$^2$ were seeded in 150 mm plates, grown to 70% confluence, treated with 0.5 nM actinomycin D for 48 h before harvest.

Northern Blot Analysis

RNA was isolated from cells approximately 70 to 100% confluent by guanidinium/cesium chloride extraction and dissolved in diethylpyrocarbonate-treated water for northern blot analysis as described previously (Han et al. (1990), "Altered levels of endogenous retrovirus-like sequence (VL30) RNA during mouse epidermal cell carcinogenesis", *Mol. Carcinogenesis* 3:75–82). A 500 base pair PstI fragment of p53-422 was used for p53 detection (Oren et al. (1983), "Molecular cloning of a cDNA specific for the murine p53 cellular tumor antigen", *Proc. Natl. Acad. Sci. USA*, 80, 56–59) and as 840 bp EcoRI-SalI fragment of pA6 was used for 7S RNA detection as a control for RNA loading (Balmain et al., (1982), "Cloning and characterization of the abundant cytoplasmic 7S RNA from mouse cells", *Nucleic Acids, Res.*, 10.4259–4277). Probes were labeled with [∝-32P|dCTP by the random primer method using a multiprime labeling kit (Amersham, Arlington Heights, Ill.). 32P-labeled probe was used at a final concentration of 1 to $2\times10^6$ cpm/ml. Differences in p53 RNA abundance were quantitated by densitometry of exposed films (Fastscan computing densitometer, Molecular Dynamics, Sunnyvale, Calif.) after adjustment for 7S RNA.

Flow Cytometry

Cells permeabilized in suspension with 100% cold ethanol were exposed to anti-p53 antibodies as described for indirect immunofluorescence above except that the secondary reagent for anti-p53as was phycoerythrin (PE)-conjugated goat anti-rabbit IgM and IgG (FisherBiotech, Pittsburgh, Pa.). Hoechst 33342 (1 µg/ml, bisbenzimide H, Calbiochem, La Jolla, Calif.) was added 1 h prior to flow analysis for detection of DNA content. Analysis was performed on a FACSTAR[+] dual 5 watt argon laser system (Becton Dickinson Immunocytometry Systems, San Jose, Calif.) with the primary laser lasing at 488 nm at 200 mW and the secondary laser lasing at 350 nm at 50 mW. PE and Hoechst emissions were passed through discretion filters with band widths of 575+/−13 nm and 424+/−22 nm, respectively. Flow cytometry data was acquired using Becton Dickinson standard acquisition software to exclude cell aggregates and debris and to collect single cell events only. Data was analyzed using Lysis II software (Becton Dickinson Immunocytometry Systems, San Jose, Calif.).

Table 1 shows response of 29.105RAT carcinoma cells to actinomycin D as detected by indirect immunofluorescence in situ. Two experiments (numbered) are shown. Cells were plated on coverslips, exposed to actinomycin D at the concentration indicated (nM) or solvent (0.2% acetone) for 48 h, then stained with p53 antibodies. Estimates of positive cells as a percentage of total cells were made based on viewing all cells per slip (10 control, 8 to 10 treated slips per experiment for p53as; 4 control, 2 to 4 treated per experiment for PAb421; 2 control and 2 treated per experiment for PAb246, pre-immune and IgG controls. The range of percent positive cells is shown for 2 independent experiments.

Table 2 shows cell cycle distribution of mouse epidermal cells according to p53 antibody reactivities. Cells were exposed to 0.5 nM actinomycin D or solvent for 2 days, harvested and stained as described in FIG. 7 and Experimental Procedures. The data shown are the mean and Std. Dev. of percentages of cells positive for each antibody based on $2\times10^6$ stained cells in 12 separate tubes (R4 negative cells or total cells), 6 tubes (anti-p53as) or 3 tubes each (PAb421 and PAb246). The results are representative of 2 separate experiments and 2 stainings of the same cell preparation. The percentage of cells in G0/G1 vs. G2/M and >G2/M were consistent among experiments within a cell type.

TABLE 1

Response of 291.05RAT epidermal tumor cells to actinomycin D detectable by indirect immunofluorescence.

| | p53 positive cells (%) | | |
|---|---|---|---|
| Treatment | PAb421 | PAb246 | αp53as |
| 1. acetone | 5–7 | 2–3 | 1–6 |
| actino D 0.5 nM | 72–75 | 57–60 | 40–60 |
| 2. acetone | 6–8 | 3–5 | 1–5 |
| actino D 0.25 nM | 25–50 | 40 | 3–5 |
| actino D 0.5 nM | 70–80 | 70–80 | 15–20 |

TABLE 2

Cell cycle distribution by flow cytometry of mouse epidermal cells according to p53 antibody reactivities.

| Cells | Treatment | Stage | (−)Cells | αp53as | PAb421 | PAb246 |
|---|---|---|---|---|---|---|
| 291LC | acetone | >G2/M | 0.6 ± 0.2 | 33 ± 6 | 4 ± 0.6 | 0.3 ± 0.2 |
| | | G2/M | 18 ± 1 | 43 ± 7 | 30 ± 3 | 34 ± 2 |
| | | S | 11 ± 1 | 9 ± 2 | 14 ± 3 | 11 ± 1 |
| | | G0/G1 | 70 ± 1 | 15 ± 2 | 52 ± 1 | 48 ± 1 |
| | | % total cells | 100 ± 0.2 | 0.5 ± 0.2 | 8 ± 2 | 3 ± 0.2 |
| 291LC | actino D | >G2/M | 0.3 ± 0.2 | 3 ± 2 | 0.5 ± 0.1 | 0.3 ± 0.2 |
| | | G2/M | 9 ± 2 | 30 ± 2 | 10 ± 1 | 11 ± 1 |
| | | S | 8 ± 0.9 | 10 ± 1 | 8 ± 0.4 | 9 ± 0.5 |
| | | G0/G1 | 83 ± 2 | 56 ± 4 | 82 ± 1 | 80 ± 1 |
| | | % total cells | 100 ± 0.6 | 2 ± 0.8 | 36 ± 3 | 12 ± 1 |
| 05RAT | acetone | >G2/M | 1 ± 0.4 | 23 ± 6 | 8 ± 1 | 6 ± 0.5 |
| | | G2/M | 19 ± 2 | 30 ± 5 | 32 ± 4 | 29 ± 1 |
| | | S | 22 ± 2 | 25 ± 5 | 24 ± 7 | 19 ± 3 |
| | | G0/G1 | 58 ± 3 | 23 ± 3 | 36 ± 5 | 46 ± 2 |
| | | % total cells | 97 ± 4 | 1 ± 0.4 | 2 ± 0.6 | 10 ± 2 |
| 05RAT | actino D | >G2/M | 1 ± 0.4 | 3 ± 3 | 1 ± 1 | 0.8 ± 0.1 |
| | | G2/M | 15 ± 3 | 40 ± 5 | 27 ± 5 | 26 ± 1 |
| | | S | 20 ± 2 | 28 ± 6 | 24 ± 5 | 25 ± 1 |
| | | G0/G1 | 64 ± 4 | 28 ± 4 | 48 ± 1 | 48 ± 1 |
| | | % total cells | 93 ± 9 | 1 ± 0.4 | 10 ± 0.1 | 23 ± 1 |

What is claimed is:

1. An antibody specific for a protein designated p53as, which protein is functionally equivalent with an active known normal growth controlling protein p53 of a mammal, the final amino acids of p53as protein proximate the carboxy terminus being sufficiently different than the carboxy terminus final 50 amino acids of the p53 protein, so that the p53as lacks a negative regulatory domain of said p53 and so that the p53as contains an epitope unique to p53as not present in said p53, said antibody being reactive with said epitope and not being reactive with said p53, said p53as functioning as a growth regulator in a manner similar to active p53 within cellular environments where said p53 loses activity due to loss of sequence specific binding by activation of said p53 negative regulatory domain.

2. The antibody of claim 1 wherein the p53as protein has an SPNC sequence in its carboxy terminal sequence (such SPNC sequence being shown in Seq. I.D. No. 1 as amino acids 14–17).

3. The antibody of claim 1 wherein the p53as protein has an SPPC sequence in its carboxy terminal sequence (such SPPC sequence being shown in Seq. I.D. No. 4 as amino acids 15–18).

4. The antibody of claim 1 wherein the antibody is a polyclonal antibody.

5. The antibody of claim 2 wherein the antibody is a polyclonal antibody.

6. The antibody of claim 3 wherein the antibody is a polyclonal antibody.

7. The antibody of claim 1 wherein the antibody is a monoclonal antibody.

8. The antibody of claim 2 wherein the antibody is a monoclonal antibody.

9. The antibody of claim 3 wherein the antibody is a monoclonal antibody.

10. The antibody of claim 1 wherein the p53as carboxy terminal sequence is longer or shorter than the 50 amino acid terminal sequence of p53.

11. The antibody of claim 1 wherein the p53as is present in normal cells of the mammal.

* * * * *